US006560492B2

(12) United States Patent
Borders

(10) Patent No.: US 6,560,492 B2
(45) Date of Patent: May 6, 2003

(54) MEDICAL EQUIPMENT CONTROLLER

(75) Inventor: Richard L. Borders, Cincinnati, OH (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 10/083,197

(22) Filed: Feb. 26, 2002

(65) Prior Publication Data

US 2002/0111701 A1 Aug. 15, 2002

Related U.S. Application Data

(62) Division of application No. 09/187,825, filed on Nov. 6, 1998, now Pat. No. 6,351,678.
(60) Provisional application No. 60/064,709, filed on Nov. 7, 1997.

(51) Int. Cl.$^7$ .............................................. G05B 11/01
(52) U.S. Cl. ................................ 700/17; 5/60; 700/83
(58) Field of Search ........................... 700/1, 2, 83, 17, 700/204, 248; 5/60, 61, 601, 613, 713, 618, 714; 600/130, 102, 118

(56) References Cited

U.S. PATENT DOCUMENTS

| 4,211,998 A | 7/1980 | Junginger et al. |
| 4,231,019 A | 10/1980 | Junginger et al. |
| 4,435,862 A | 3/1984 | King et al. |
| 4,680,790 A | 7/1987 | Packard et al. |
| 4,712,105 A | 12/1987 | Kohler |
| 4,745,647 A | 5/1988 | Goodwin |
| 4,769,584 A | 9/1988 | Irigoyen et al. |
| 4,825,200 A | 4/1989 | Evans et al. |
| 4,850,040 A | 7/1989 | Teich et al. |
| 4,999,622 A | 3/1991 | Amano et al. |
| 5,072,463 A | 12/1991 | Willis |

(List continued on next page.)

FOREIGN PATENT DOCUMENTS

| CH | 675936 | 11/1990 |
| EP | 0 316 643 | 5/1989 |
| EP | 0 348 726 | 1/1990 |
| EP | 0 373 912 | 6/1990 |
| EP | 0 455 852 | 11/1991 |
| EP | 0 488 552 | 6/1992 |
| EP | 626635 | 11/1994 |
| JP | 5-95978 | 4/1993 |

*Primary Examiner*—Leo Picard
*Assistant Examiner*—Kidest Bahta
(74) *Attorney, Agent, or Firm*—Bose McKinney & Evans LLP

(57) ABSTRACT

A patient support system comprises an articulated frame having a plurality of segments, a frame controller coupled to the frame to move at least one of the segments, a mattress having at least one chamber, a mattress controller coupled to the mattress to control an amount of fluid in the at least one chamber, and a user interface controller configured to send control signals to the frame controller and to the mattress controller.

34 Claims, 15 Drawing Sheets

U.S. PATENT DOCUMENTS

| | | |
|---|---|---|
| 5,073,999 A | 12/1991 | Thomas et al. |
| 5,235,713 A | 8/1993 | Guthrie et al. |
| 5,239,300 A | 8/1993 | Berger et al. |
| 5,251,349 A | 10/1993 | Thomas et al. |
| 5,410,326 A * | 4/1995 | Goldstein .............. 340/825.72 |
| D362,660 S | 9/1995 | Fromson |
| D363,552 S | 10/1995 | Teo et al. |
| 5,509,154 A | 4/1996 | Shafer et al. |
| 5,542,136 A | 8/1996 | Tappel |
| 5,542,138 A | 8/1996 | Williams et al. |
| 5,544,376 A | 8/1996 | Fromson |
| 5,600,214 A | 2/1997 | Fromson |
| 5,611,096 A | 3/1997 | Barlett et al. |
| 5,627,584 A | 5/1997 | Nishikori et al. |
| 5,652,484 A | 7/1997 | Shafer et al. |
| D382,543 S | 8/1997 | Tsung |
| D382,645 S | 8/1997 | Bergeron |
| 5,664,270 A | 9/1997 | Bell et al. |
| 5,678,568 A | 10/1997 | Uckikubo et al. |
| 5,754,997 A | 5/1998 | Lussi et al. |
| 5,759,149 A * | 6/1998 | Goldberg et al. ............. 600/22 |
| 5,771,511 A | 6/1998 | Kummer et al. |
| 5,787,528 A | 8/1998 | Antinori |
| 5,815,864 A | 10/1998 | Sloop |
| 5,815,865 A * | 10/1998 | Washburn et al. ............. 5/706 |
| 5,983,429 A | 11/1999 | Stacy et al. |
| 6,038,718 A | 3/2000 | Penninig et al. |
| 6,135,949 A | 3/2000 | Russo et al. |
| 6,117,076 A | 9/2000 | Cassidy |
| 6,131,868 A * | 10/2000 | Welling et al. .......... 248/276.1 |
| 6,163,903 A | 12/2000 | Weismiller et al. |
| 6,336,235 B1 | 1/2002 | Ruehl |
| 6,353,950 B1 * | 3/2002 | Bartlett et al. ................. 5/609 |

* cited by examiner

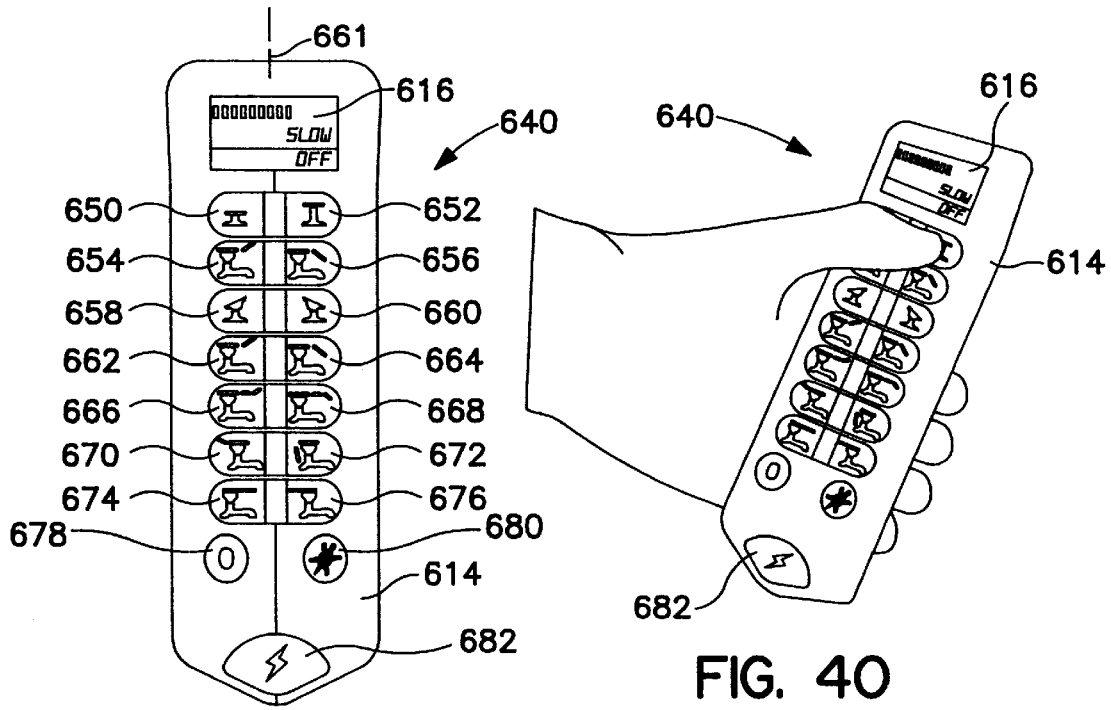
FIG. 39
FIG. 40
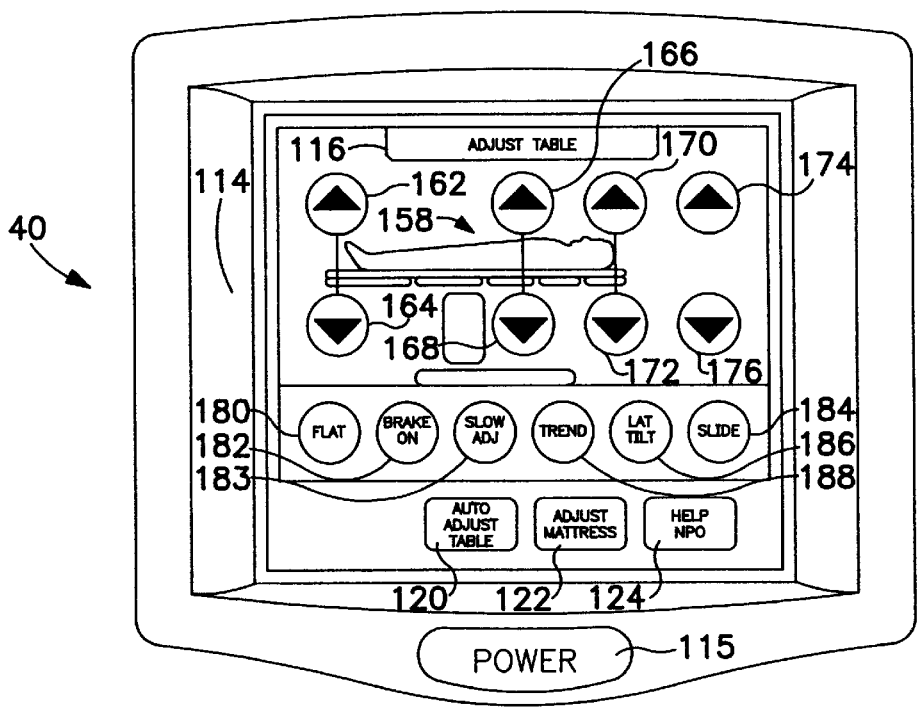
FIG. 13B

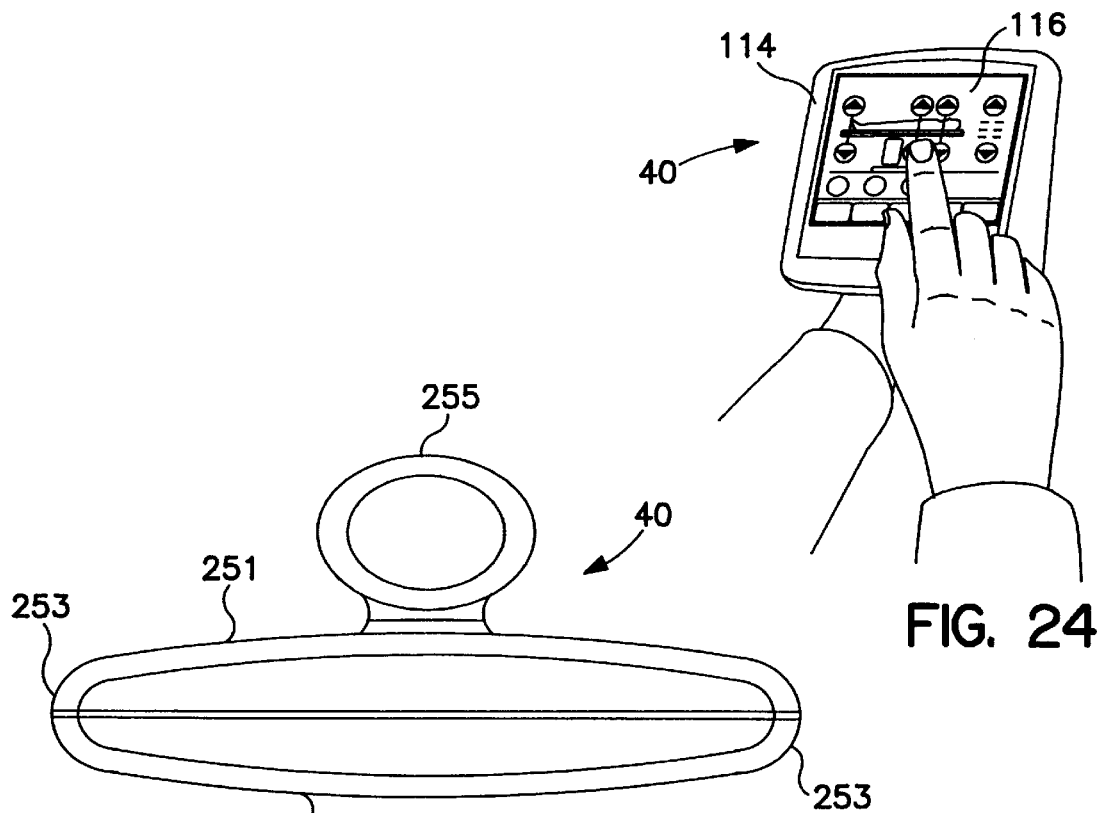
FIG. 24
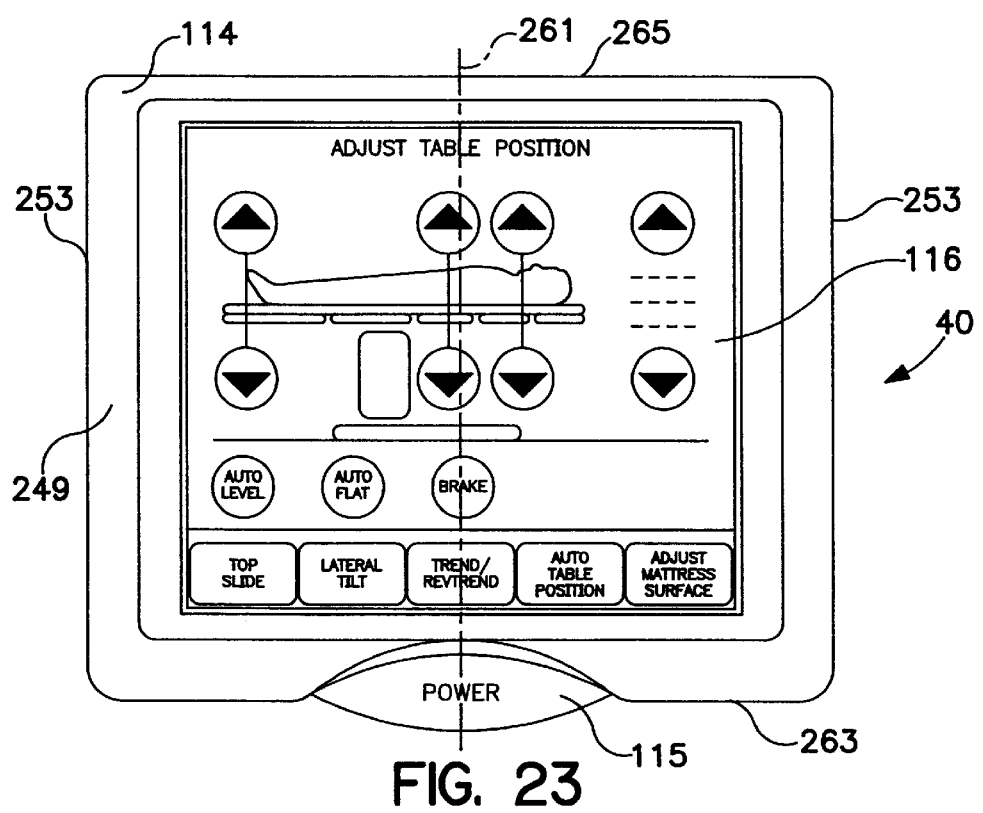
FIG. 22
FIG. 23

MEDICAL EQUIPMENT CONTROLLER

This application is a divisional of U.S. application Ser. No. 09/187,825, filed Nov. 6, 1998, now U.S. Pat. No. 6,351,678, which claims the benefit of U.S. provisional application Serial No. 60/064,709 filed Nov. 7, 1997, the disclosures of which are incorporated by reference herein.

BACKGROUND AND SUMMARY OF THE INVENTION

The present invention relates generally to device controllers, and particularly to device controllers for remote control of one or more pieces of medical equipment. More particularly, the present invention relates to medical device controllers for control of operating room equipment such as an articulated surgical table and a controllable mattress that is coupled to the articulated table.

Many medical devices are controllable, such as surgical tables with articulated support surfaces that use motors to adjust the support surfaces to desired configurations. Other examples include mattresses with multiple fluid chambers and systems for controlling fluid pressures within the chambers, or mattresses with vacuum beads for conforming the mattress surface to a patient. Similarly, surgical light systems are often controllable to vary the intensity and direction of a light source. A patient support system or treatment device can also include a controllable temperature subsystem, such as a resistive mattress cover, or a mechanism to control fluid temperature in a fluid-based mattress system, etc. Each controllable system typically includes its own separate control having multiple buttons, programming modes, and display configurations. An operator or care giver desiring to control each of these controllable systems must understand and operate the interface schemes for all of the associated controllers.

According to the present invention, a medical device controller for controlling a surgical table is provided. The surgical table has a controllable articulated frame and a controllable surface coupled to the frame. The medical device controller includes a housing configured to be hand-held, a display coupled to the housing, and a processor coupled to the display. The processor is configured to provide indicia on the display indicative of a user command to move the articulated frame to a desired frame configuration. The processor is further configured to command the articulated frame to move to the desired frame configuration based on a user input. The processor is furthermore configured to provide indicia on the display indicative of a user command to adjust the controllable surface to a desired surface configuration and to command the surface to adjust to the desired surface configuration based on a user input.

In illustrative embodiments, the processor is configured to provide a menu on the display of predefined configurations of the articulated frame and to command the articulated frame to move to a selected one of the predefined configurations based on a user input. The processor includes a user interface for accepting the user input to select one of the predefined configurations.

Further illustratively, the menu includes a plurality of named positions that correspond to predefined configurations. The processor is configured to provide an iconographic representation on the display indicative of the articulated frame. The iconographic representation includes a representation indicative of an adjustment of the articulated frame. An input device is provided near the representation indicative of an adjustment, and the processor is configured to adjust the articulated frame based on a user input to the input device when the representation indicative of an adjustment is provided on the display.

In other illustrative embodiments, the processor is further configured to provide a representation on the display indicative of an automatic adjustment of the articulated frame to a predefined configuration based on a current configuration of the articulated frame. An input device is provided near the representation indicative of an automatic adjustment. The processor is configured to adjust the articulated frame to the predefined configuration based on a user input to the input device when the representation indicative of an automatic adjustment is provided on the display.

Further illustratively, the processor is configured to provide a menu on the display of additional functions to permit adjustment of the articulated frame and to provide a second iconographic representation of the articulated frame on the display based on a selection of a function from the menu of additional functions. The second iconographic representation includes a representation indicative of a user input for adjustment of the articulated frame. An input device is provided near the indicative representation. The processor is configured to adjust the articulated frame based on a user input to the input device when the indicative representation is provided on the display.

In still other illustrative embodiments, the device controller housing is substantially symmetric about an axis. The articulated frame is a surgical table frame and the controllable surface is a mattress that includes a plurality of controllable fluid chambers. The processor can further be configured to command a temperature control system and/or a lighting system. The processor can be configured to communicate using a wireless communications protocol. The processor can be configured to signal an alert if a distance between the processor and a base unit exceeds a predefined distance.

Further illustratively, the processor includes an audio input module that receives audible user input signals. The processor is configured to provide a menu on the display of predefined configurations of the articulated frame and to select one of the predefined configurations based on an input from the audio input module. The processor is configured to provide an iconographic representation on the display indicative of the articulated frame including a representation indicative of an adjustment of the articulated frame. The processor is configured to adjust the articulated frame based on an input from the audio input module when the representation indicative of an adjustment is provided on the display.

In yet still other illustrative embodiments, the processor is configured to provide a medical device controller tutorial menu on the display based on selection of a user input. The display defines a plane and a user input device that is coupled to the processor is provided adjacent the display in a location normal to the plane of the display. A sterile cover configured to surround the housing that is sufficiently translucent to allow visual perception of indicia on the display through the cover is also provided.

According to other aspects of the invention, a medical device controller having a housing configured to be hand-held and a display coupled to the housing is provided. A user input device is coupled to the housing. A processor is coupled to the display and configured to provide a representation on the display near the user input device indicative of a command to a controllable device. The processor commands the controllable device based on a user input to the user input device.

In illustrative embodiments, a switch is provided to a side of the display and the representation on the display indicative of a user input is displayed near the side of the display. Alternatively, the user input device is a touch screen input of the display. Illustratively, the controllable device is an articulated surgical table. The processor is further configured to control a separately controllable surface having a plurality of controllable fluid chambers. The processor is further configured to command a patient thermal regulation system and/or a lighting system.

Further illustratively, the processor is coupled to an audio input module that receives audible user input signals. The processor is configured to provide a menu on the display of predefined configurations of the articulated frame and to command the articulated frame to move to a selected one of the predefined configurations based on a user input. The processor is configured to select one of the predefined configurations based on an input from the audio input module.

According to still other aspects of the invention, a medical device controller includes a housing configured to be hand-held, a display coupled to the housing, a user input device coupled to the housing, and a processor coupled to the display. The processor is configured to command a controllable medical device, to provide on the display an iconographic representation of the controllable device, to provide a representation on the display near the user input device indicative of a command to the controllable device, and to command the controllable device based on a user input to the user input device.

According to yet other aspects of the invention, a medical device controller includes a housing configured to be hand-held, a display coupled to the housing, a user input device coupled to the housing, and a processor coupled to the display. The processor is configured to command a controllable medical device, to provide a menu on the display of predefined configurations of the controllable device, and to command the controllable device to a predefined configuration from the menu based on a user input to the user input device.

According to still yet other aspects of the invention, a medical device controller includes a housing configured to be hand-held. The housing has a front side and a back side and is substantially symmetric about an axis. A display is coupled to the front side of the housing and a user input device coupled to the housing. A processor is coupled to the display. The processor is configured to command a controllable medical device, to provide a menu on the display of predefined configurations of the controllable device, and to command the controllable device to a predefined configuration from the menu based on a user input to the user input device.

In illustrative embodiments, the housing includes an appendage coupled to the back side configured to be retained by a complementary socket so that the housing can be removably coupled to an apparatus having the complementary socket. Further illustratively, the appendage comprises a generally cylindrical handle.

According to other aspects of the invention, a medical device controller includes a housing configured to be hand-held, a display coupled to the housing, and a user input device coupled to one of the display and the housing. A processor is coupled to the housing and to the display. The processor is configured to command a controllable medical device, to determine if a predetermined distance from a base unit is exceeded, and to signal an alert if the processor determines the predetermined distance from the base unit is exceeded. Illustratively, the alert is an audible alarm.

According to still other aspects of the invention, a medical device controller includes a housing configured to be hand-held, a display coupled to the housing, and a user input device coupled to one of the display and the housing. A processor is coupled to the display. The processor is configured to command a controllable medical device based on a user input to the user input device and to provide a tutorial guide for operation of the controllable medical device.

According to yet other aspects of the invention, an operating room table system includes an articulated frame having a plurality of segments. A frame controller is coupled to the frame to move at least one of the segments. A mattress having at least one chamber is provided. A mattress controller is coupled to the mattress to control an amount of fluid in the at least one chamber. A user interface controller is configured to send control signals to the frame controller and to the mattress controller.

According to still yet other aspects of the invention, an operating room table system includes an articulated table having a plurality of segments. A table controller is coupled to the table to move at least one of the segments. A lighting system having at least one light head is provided. A lighting controller is coupled to the lighting system to control an intensity of light from the at least one light head. A user interface controller is configured to send control signals to the table controller and to the lighting controller. Instead of or in addition to the lighting system, a patient thermal regulation system is provided. A thermal regulation controller is coupled to the patient thermal regulation system. The user interface controller is configured to send control signals to the table controller and to the thermal regulation controller.

Additional features of the invention will become apparent to those skilled in the art upon consideration of the following detailed description of the presently perceived best mode of carrying out the invention.

BRIEF DESCRIPTION OF THE DRAWINGS

The detailed description particularly refers to the accompanying figures in which:

FIG. 13B is a front elevation view of the medical device controller of FIG. 9, showing an adjust table screen somewhat similar to FIG. 13A, with Trendenlenberg, lateral tilt, and slide selection indicators positioned adjacent auto flat, brake, and slow adjust input indicators, and automatic table adjustment, mattress adjustment, and help information selection indicators along the bottom of the display;

FIG. 22 is a top plan view of an embodiment of a medical device controller similar to the embodiment of FIGS. 9–11, showing a relatively slim housing profile that is symmetric about a longitudinal axis and a generally cylindrical handle appended to a central portion of a back surface of the housing to facilitate storage and ambidextrous use of the controller;

FIG. 23 is a front elevation view of the controller of FIG. 22 showing a power button and a display;

FIG. 24 is a perspective view of the controller of FIG. 22 showing a user holding the controller with one hand and entering commands on the touch-screen with the other hand;

FIG. 39 is a front elevation view of yet another embodiment of a medical device controller, showing a hand-held housing, a display, and several pairs of control buttons, each pair of buttons aligned along a central vertical axis of the housing to facilitate ambidextrous use of the controller; and FIG. 40 is a perspective view of the controller of FIG. 39 showing left-handed use of the controller.

DETAILED DESCRIPTION OF DRAWINGS

Figure 1:
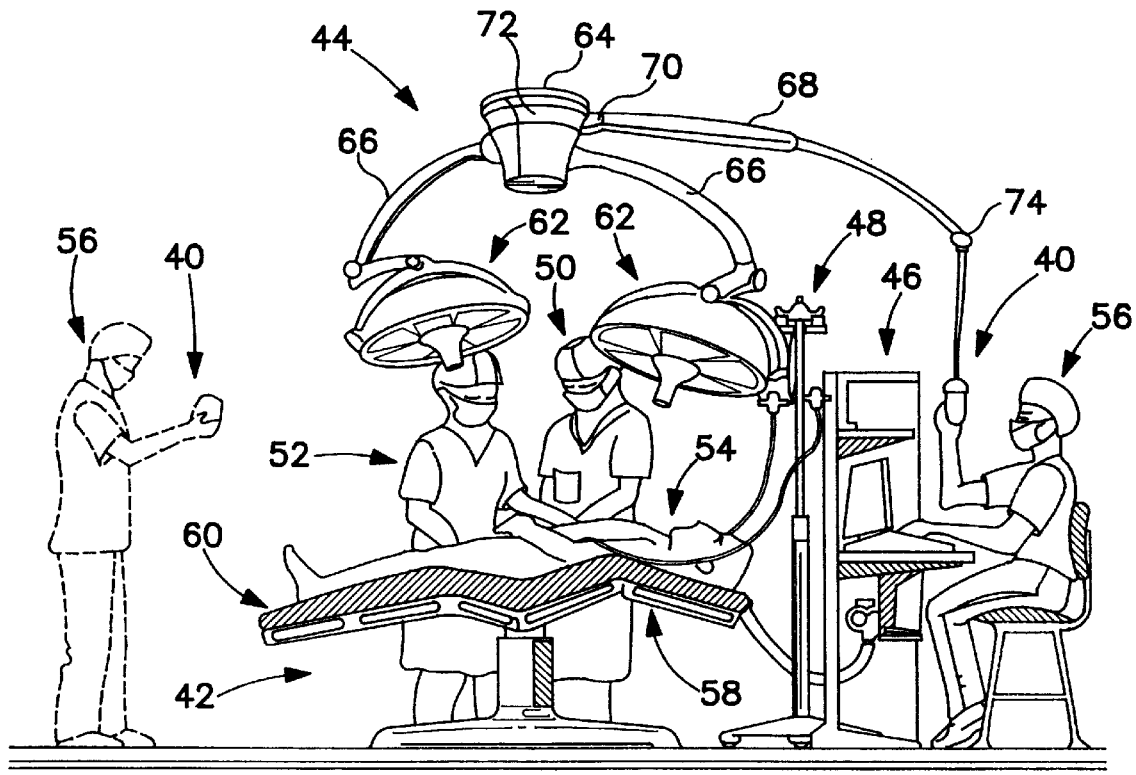
FIG. 1 is perspective view of an operating room environment showing a patient positioned atop a surgical table including an articulated frame and a mattress, a lighting system having a base unit and two light heads independently coupled to the base unit by articulated arms, an IV stand with a pair of IV bags coupled to the patient, a control station with a computer system interface to the surgical table, and a first medical device controller integrated with the operating room environment and coupled to the lighting system base unit by a telescoping and pivoting arm system and a second medical device controller shown with dashed lines integrated with the operating room environment and using a wireless communications link.

A medical device controller 40 according to the present invention is integrated into an operating room environment that includes a surgical table 42, a surgical lighting system 44, a control station 46, and an IV stand 48, as shown in FIG. 1. A surgeon 50 and one or more assistants 52 typically perform a procedure on a patient 54 while another care giver 56, such as an anesthesiologist or a nurse, controls and monitors operating room equipment from control station 46. Table 42 and lighting system 44 provide a variety of controllable features, as discussed in more detail below. Controller 40 provides a single, integrated, user-friendly interface for care giver 56 to control medical devices such as table 42 and lighting system 44.

Controller 40 is a hand-held device and can be configured to control medical devices through a variety of communication interfaces. For example, as shown in FIG. 1, lighting system 44 includes a base unit 64 coupled to light heads 62 via independent, articulated arms 66. Controller 40 can be coupled directly to based unit 64 by a telescoping arm 68. Telescoping arm 68 is coupled to base unit 64 by a horizontal pivot 70 and a vertical pivot 72, and includes a distal pivot 74, thereby providing for flexible movement of controller 40 throughout the operating room environment. In this configuration, signals between controller 40 and light heads 62 can be hard-wired through arms 66, 68 and base unit 64.

Controller 40 is either wired directly to the controllable devices or, preferably, is configured to send signals to the controllable devices using a wireless link, such as a radio frequency (RF) or infrared (IR) communication link. Wireless communication links are well-known to those of ordinary skill in the art. Thus, it is within the scope of the present invention for controller 40 to use any means known to those skilled in the art to send signals to the controllable devices.

By using a wireless communication protocol, controller 40 is conveniently moved around the operating room environment by care giver 56, for example as shown by dashed lines in FIG. 1. A sterile sheath (not shown), made from a suitably flexible and transparent material such as thin latex rubber, is provide to encapsulate controller 40 so that it can be safely used throughout an operating room without contaminating the sterile environment. By providing a single controller 40 that integrates controls for several operating room devices, and allowing controller 40 to be moved freely throughout the environment, the present invention increases operating room efficiency.

Figure 2:
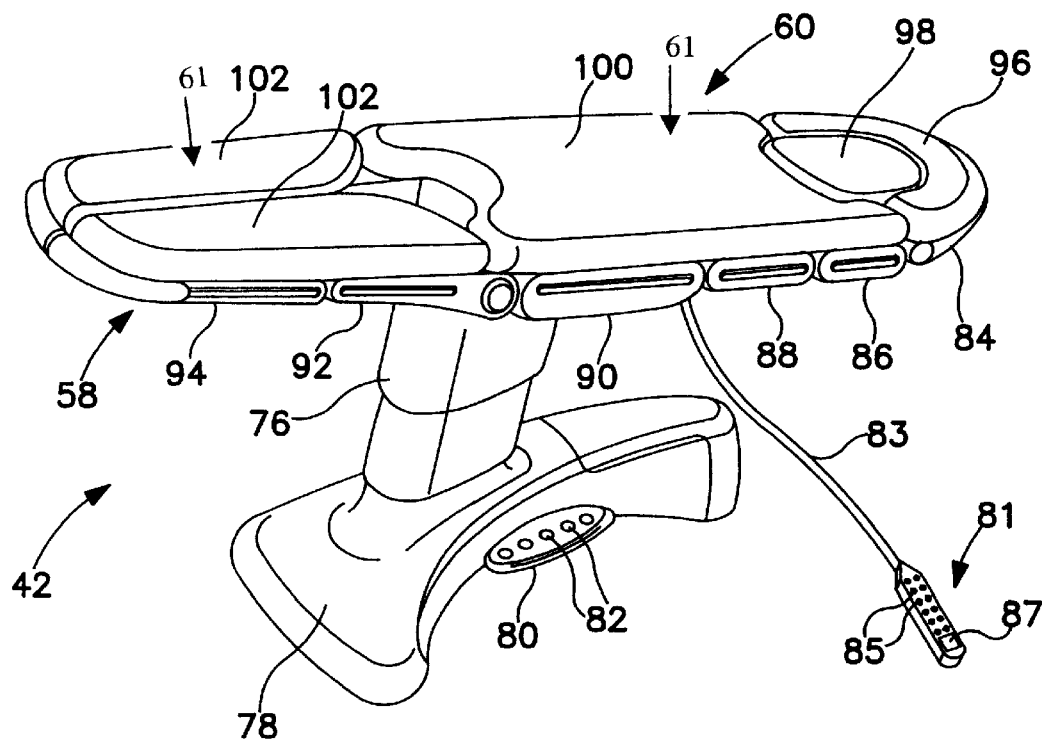
FIG. 2 is a perspective view of a controllable surgical table of the type shown in FIG. 1, including a base having foot controls, a vertically adjustable support column coupled to the base, an articulated frame coupled to the support column, a segmented mattress system supported by the articulated frame, and a pendant remote controller for controlling surgical table functions.
Figure 3:
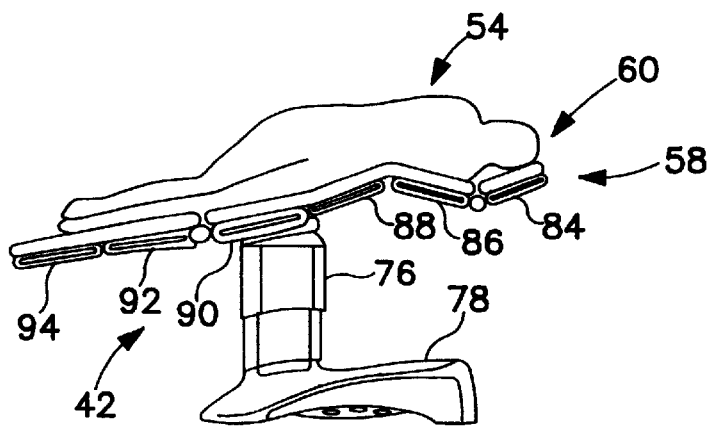
FIGS. 3–6 are side elevation views of the controllable surgical table of FIG. 2, showing the adjustable support column and articulated frame configured to support a patient in lateral, sitting, proctological, and lithotomy configurations for various medical or surgical procedures.
Figure 4:
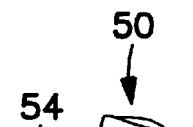
Figure 5:
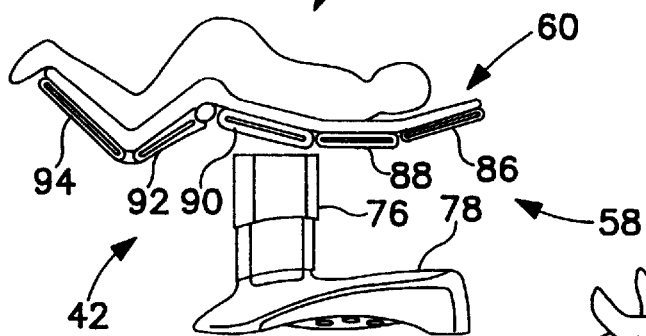
Figure 6:
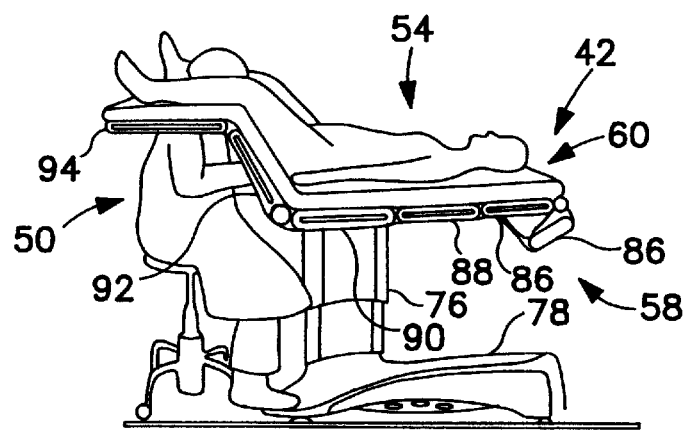

Modern surgical tables such as the illustrative table 42 shown in FIGS. 1–6 provide a variety of controllable functions. Table 42 includes articulated table frame 58, mattress 60, vertical support column 76, and base 78. Base 78 includes a foot control panel 80 having a plurality of control buttons 82, for adjusting vertical support column 76, mattress 60, and articulated table frame 58. As shown in FIG. 2, a pendant controller 81 coupled by a tether 83 to frame 58 similarly includes a plurality of control buttons 85 as well as a display 87. Pendant controller 81, which can be coupled to table 42 at any convenient location, similarly provides for adjusting frame 58, mattress 60, and support column 76.

Articulated table frame 58 includes a head section 84, an upper back section 86, a lower back section 88, a seat section 90, a pair of upper legs section 92, and a pair lower legs section 94. Sections of table frame 58 are coupled to longitudinally adjacent sections via pivots so that adjacent sections can be rotated with respect to each other by motors (not shown) or other suitable actuators well-known to those skilled in the art. Support column 76 is similarly vertically adjustable by a motor or actuator (not shown). Adjustment of articulated table frame sections 84, 86, 88, 90, 92, 94, and vertical support column 76 can be controlled by buttons 82 or, as discussed in more detail below, via controller 40.

Mattress 60 illustratively includes an outer head section 96, an inner head section 98, a torso section 100, and a pair of legs section 102. Torso section 100 and legs section 102 illustratively include a plurality of chambers 61 that are individually controllable. Mattress 60 can be any type of controllable mattress surface, e.g., some type of fluid mattress such as an air mattress, or a vacuum bead mattress, etc. In the context of the embodiments of the invention as discussed below, mattress 60 illustratively is a vacuum bead air mattress system in which mattress sections 96, 98, 100, and 102 can include multiple chambers and are coupled to a pressure and vacuum system to allow for selectively controlling the amount of pressure or vacuum in any chamber within any of the sections. Mattress 60 also includes a plurality of pressure sensors (not shown) to allow for measuring pressure within any chamber of the mattress sections. An illustrative controllable mattress is disclosed in U.S. Pat. No. 5,966,763, entitled "Surface Pad System for a Surgical Table", which is hereby incorporated by reference.

Surgical table 42 can be placed into configurations to support various medical or surgical procedures as shown, for example, in FIGS. 3–6. As discussed in more detail below, controller 40 provides for automatically placing table 42 in a desired, predefined configuration, such as those shown in FIGS. 3–6, as well as for incrementally adjusting table frame 58 and mattress 60 as required to accommodate variations needed for any particular doctor 50 or patient 54.

Features of controllable tables such as surgical table 42 are also discussed and shown in detail in U.S. Pat. Nos. 6,073,284; 6,149,674; and 6,202,230, all of which are hereby incorporated by reference.

Figure 7:
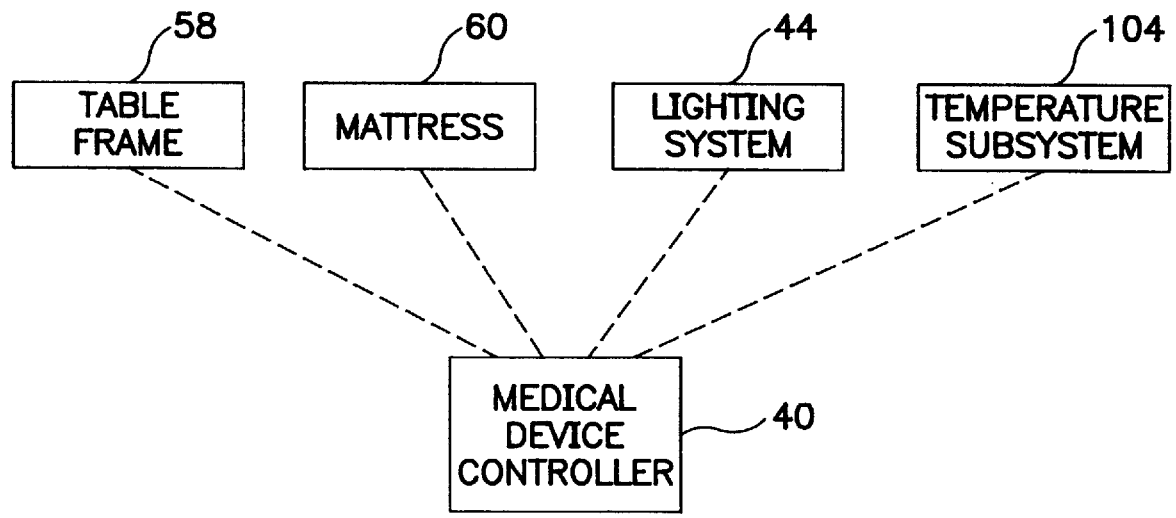
FIG. 7 is a block diagram showing interfaces between a medical device controller according to the present invention and a surgical table, mattress surface, heating subsystem, and lighting system.
Figure 8:
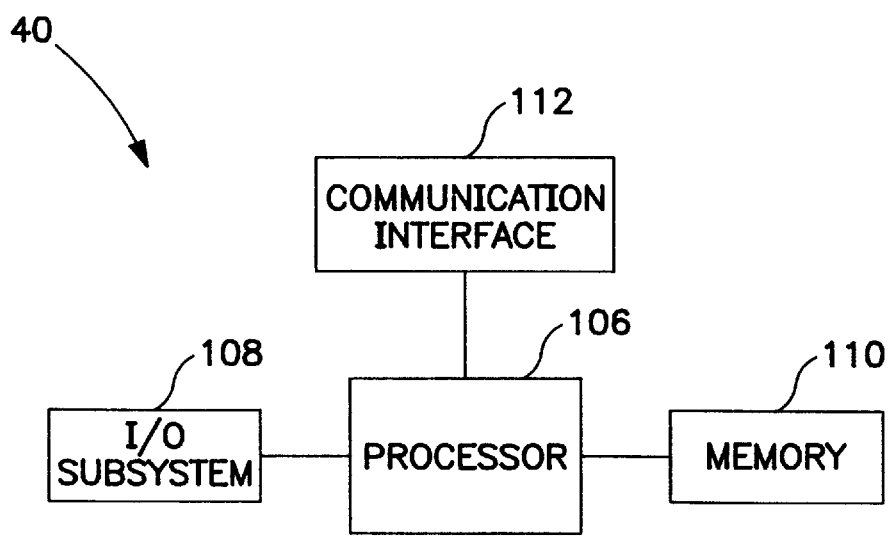
FIG. 8 is a block diagram showing an architecture of the medical device controller of FIG. 7, showing a processor coupled to display, user input, and device communication subsystems.

As illustrated by the block diagram of FIG. 7, controller 40 provides a single, mechanism for an operator, such as care giver 56, to control features of articulated frame 58 or mattress 60 of surgical table 42, as well as other controllable systems such as a lighting system 44 or a temperature control subsystem 104 that can be integrated with mattress 60. As shown in FIG. 8, a basic architecture for controller 40 can be a processor 106 that is coupled to an I/O subsystem 108, a memory 110, and a communication interface 112. Processor 106 is illustratively a microprocessor or a microcontroller (the latter can include integral memory to alleviate the need for a separate memory 110.) By providing a processor-based architecture with memory 110, controller 40 can be reconfigured or reprogrammed as needed to provide for control of new or different controlled medical devices, user interface needs, or external interface requirements. It is only necessary for a controlled device to be compatible with communication interface 112 as provided with controller 40.

Controller 40's I/O subsystem 108 is illustratively a touch-screen display system which provides a backlit, liquid crystal display 116. The touch screen input signals are illustratively provided by a matrix of translucent, membrane-type switches (not shown) positioned above display 116, although any touch-screen technology known to those skilled in the art can be used, such as those provided with personal digital assistant devices such as an Apple Newton™ or PalmPilot™ devices. Furthermore, although a touch-screen display is preferred for I/O subsystem 108, a display with buttons or switches arranged near the display screen is also contemplated.

Communication interface 112 illustratively is a pulsed infrared communication system, which technology is well known in the art. Table 42 is coupled to an IR receiver system (not shown) that provides for receiving IR signals from controller 40 for commanding frame 58 and mattress 60 based on received IR command signals. As discussed above, a hard-wired communication link can be used, or other wireless communication systems can be used, such as an RF-based system, or an ultrasound system, or any other type of wireless technology. Communication interface 112 can also be configured to support multiple communication protocols or interfaces, for example by including a hard-wired connection to support one controlled subsystem and an infrared connection to support other controlled subsystems.

Figure 9:
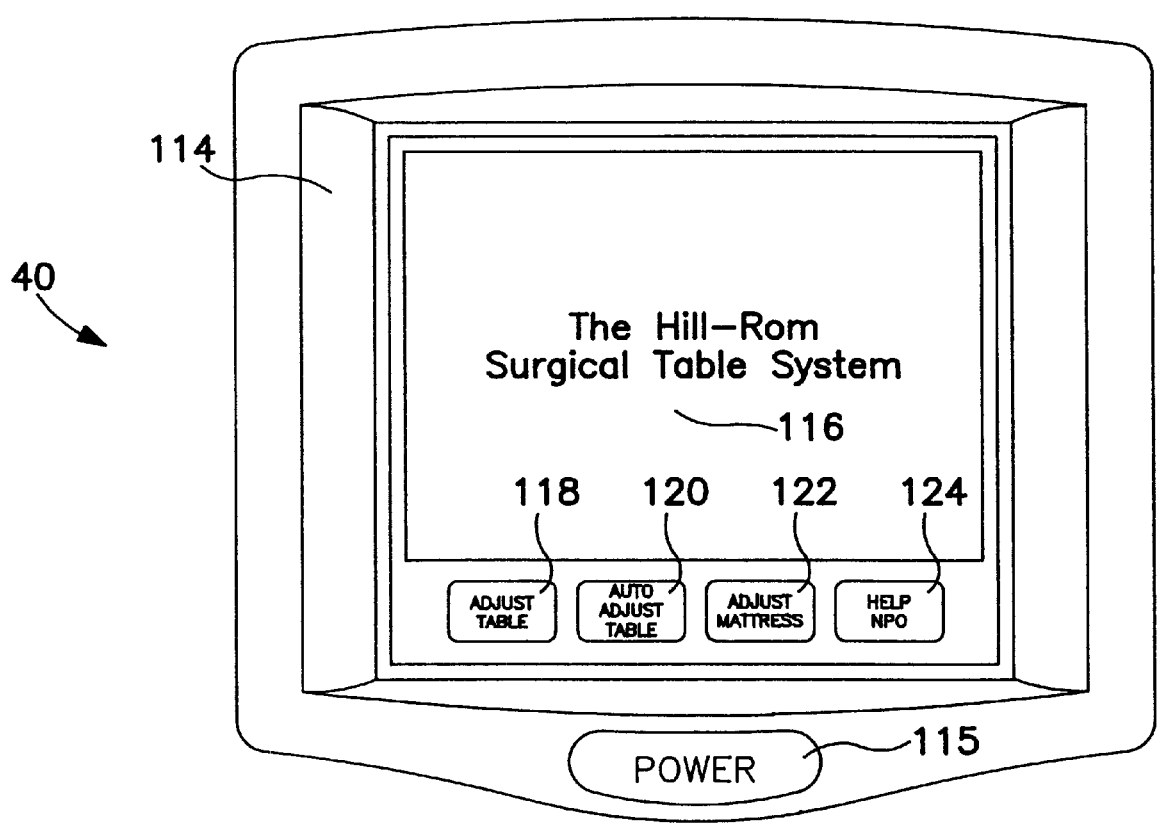
FIG. 9 is a front elevation view of a medical device controller according to the present invention showing a power button and a touch-screen display presenting an introductory menu with selection indicators for accessing controller functions to adjust a surgical table, to automatically adjust the table to predefined configurations, to adjust a mattress, or to obtain help from an on-line information guide.

Referring now to FIG. 9, controller 40 includes a housing 114, a power button 115, and a touch-screen display 116. Controller 40 is a hand-held unit that includes microprocessor or microcontroller 110 programmed to control a surgical table system such as that shown in FIGS. 1–6 via an IR or RF communication link 112 and to provide the user interface displays as shown in FIGS. 9–21. Controller 40 is powered on by depressing power button 115, whereupon the introductory display shown in FIG. 9 is provided, which includes four touch-screen selection indicators 118, 120, 122, 124 to designate to an operator access to further display interfaces for surgical table adjustment, automatic table adjustment, mattress adjustment, or accessing help information, respectively. Selection indicators 118, 120, 122, 124 are provided above touch-screen input switches included in touch-screen display 116 such as membrane switches (not shown), although, again, other touch-screen technologies can be used, or selection indicators 118, 120, 122, 124 can be positioned near buttons or switches provided along edges of display 116.

Figure 10:
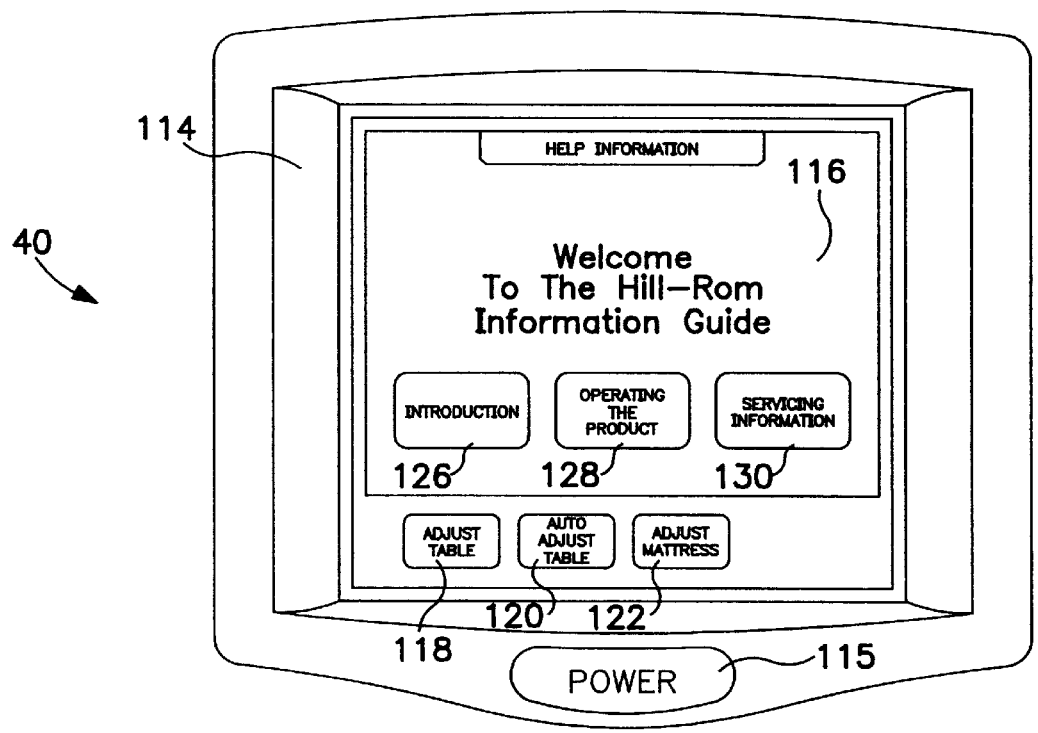
FIG. 10 is a front elevation view of the medical device controller of FIG. 9, showing a display accessed via the help selection, with selection indicators provided for obtaining introductory help information, operating instructions for controllable devices, and servicing information.

Controller 40 includes software programmed so that access of help information via selection indicator 124 from the display of FIG. 9 yields display of the help information screen of FIG. 10. Help information selection indicator 124 is removed, and more detailed help-related selection indicators 126, 128, 130 are provided for designating access to introduction, product operation, and servicing information screens. These detailed help screens provide on-line information that an operator otherwise would typically need to consult printed manuals to obtain.

Introduction screens accessed via selection indicator 126 provide information on the use and capabilities of controller 40, while product operation screens accessed via selection indicator 128 provide tutorial information on the use and capabilities of controlled systems such as table 42. Servicing information screens accessed via selection indicator 130 provide both manual and automated service and diagnostic facilities. Automated features include internal diagnostics of controller 40 and reporting of any diagnostic or service information available from controlled systems such as table 42. Controller 40 can provide "built-in-test" screens that will exercise controlled systems and either automatically verify proper operation or prompt an operator to perform a verification. Controller 40 can automatically recognize required servicing information from any controlled device capable of reporting such information, and provide recommendations to the operator accordingly. By providing menu-based, on-line information for aspects of controller 40's operation and servicing, as well as providing on-line information on controlled systems such as table 42, controller 40 provides care givers with an efficient, user-friendly, integrated interface.

Figure 11:
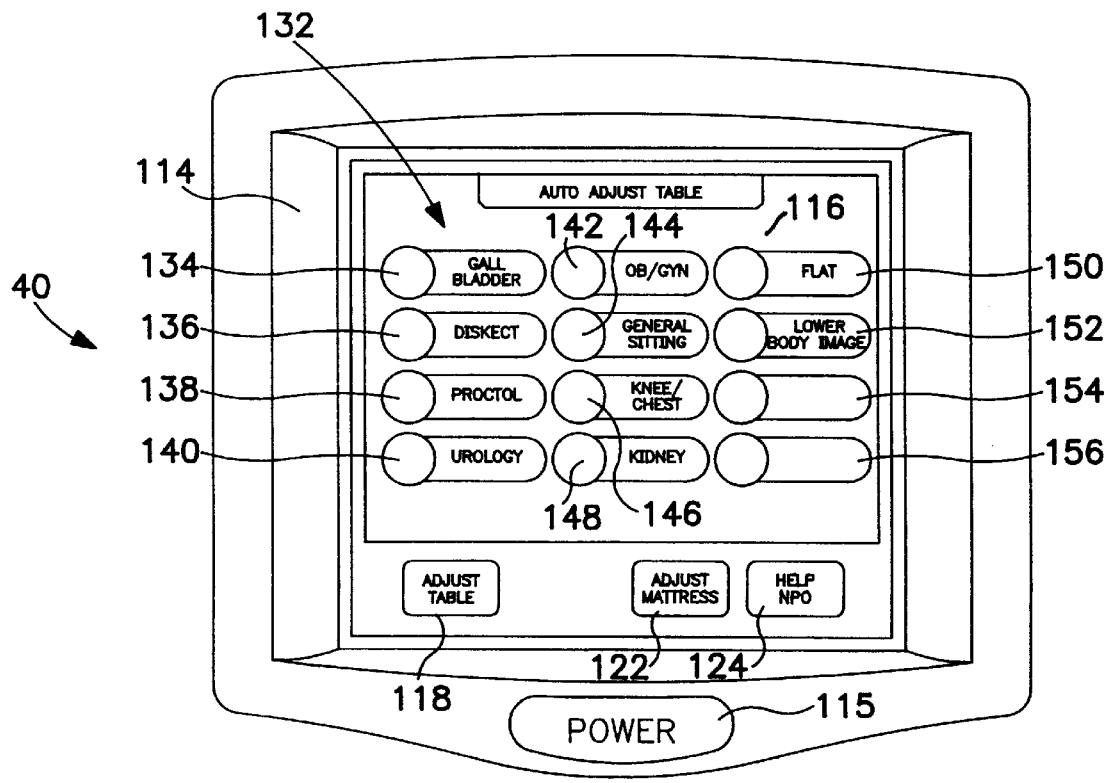
FIG. 11 is a front elevation view of the medical device controller of FIG. 9, showing a menu display accessed via the automatically adjust selection, with selection indicators provided for selecting table configurations described by surgical procedures.

Controller 40 includes software programmed so that selection via automatic table adjustment selection indicator 120 from the display of FIG. 9 yields display of an auto adjust table screen as shown in FIG. 11. Automatic table adjustment selection indicator 124 is removed and a descriptive menu 132 is provided for selecting various predefined configurations of surgical table 42. Menu 132 illustratively provides matrix of named table configurations 134 . . . 156, in which each configuration includes text descriptive of a surgical procedure or category placed next to a button symbol.

Figure 21:
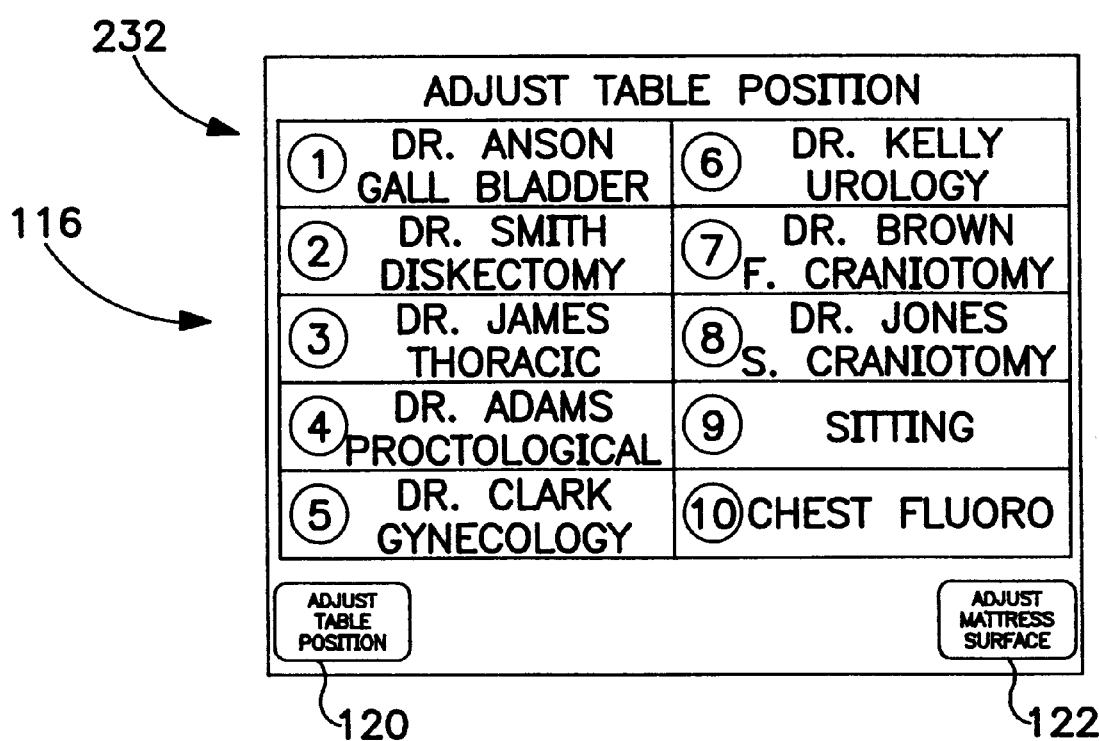
FIG. 21 is a front view of an alternative embodiment menu display similar to FIG. 11 with selection indicators provided for selecting predefined surgical table configurations described by doctor's names and/or surgical procedures.

An operator selects a configuration by pressing the adjacent button symbol, which is positioned on touch-screen display 116 above a touch-screen input switch. The descriptive text itself can be placed above one or more switches to achieve the same function by having the operator press directly above the text. The descriptive text can also be alternatively displayed near a button coupled to the housing along an edge of display 116. An alternative automatic table adjustment menu 232 is shown in FIG. 21, in which display 116 is partitioned into two columns each having five named table positions, with text that describes a medical or surgical configuration and in some cases an doctor's name. Although two columns of five named table positions are shown, the invention contemplates an arbitrary number of menu entries which can be presented on multiple screens or with a scrolling function. Alternative menu 232 illustrates how controller 40's display and processor-based architecture facilitates modifications of the user interface.

Figure 12:
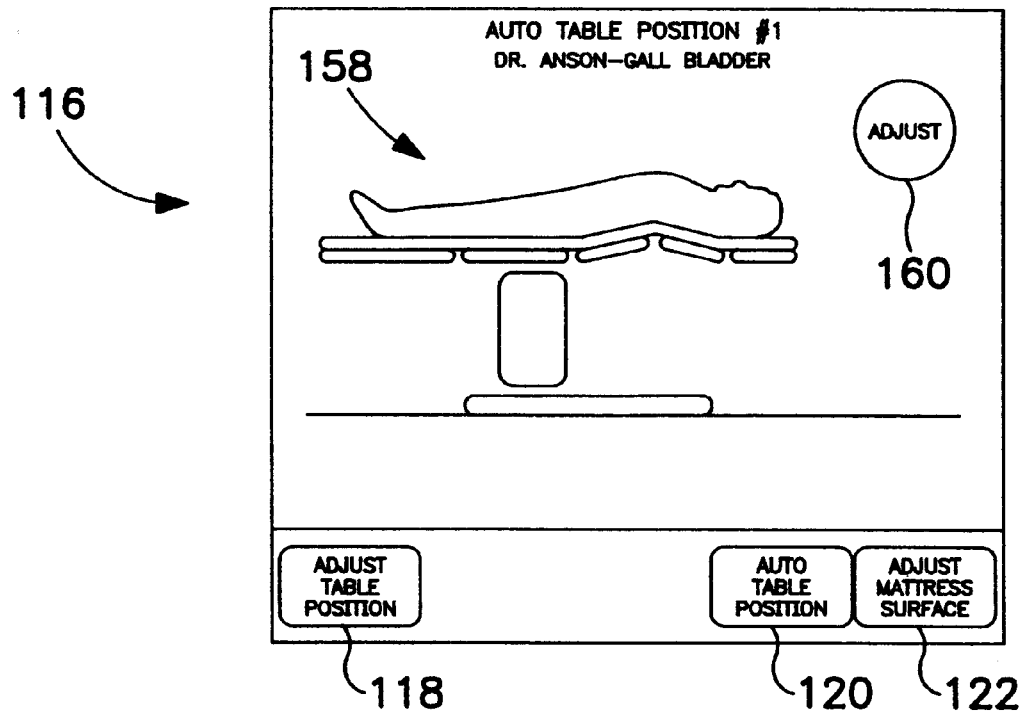
FIG. 12 is a front view of a display of a medical device controller similar to the display of FIGS. 9–11, showing an automatic configuration screen accessed from a menu selection such as provided by FIG. 11, the screen including an iconographic representation of a side view of a patient atop a mattress surface and articulated table frame configured consistently with the surgery description, and a selection indicator for an operator to automatically configure the table to the configuration corresponding to the iconographic representation.

Referring now to FIG. 12, a screen on display 116 based upon a selection of configuration 134, 234 from menu 132, 232 as shown in FIG. 11 or 21 is shown. An iconographic representation or pictogram 158 of a predetermined configuration of table 42 suitable for a gall bladder procedure, along with an adjust input indicator 160, are provided. Selection indicators 118, 120, 122 to designate access to table adjustment, automatic table adjustment, and mattress adjustment displays, respectively, are also provided.

Iconographic representation 158 provides a graphical depiction in outline form of table 42 as configured for a gall bladder procedure, including patient 54, mattress 60, sections 86, 88, 90, 92, 94 of articulated table frame 58, vertical support column 76, and base 78. If an operator wants to adjust table 42 automatically to the gall bladder configuration as depicted in iconographic representation 158, then the operator simply presses touch screen 116 above adjust input indicator 160. Software in controller 40 is configured to command table 42 to move to the predefined configuration only while a touch input is provided above adjust input indicator 160. This "press and hold" feature provides a safety interlock in that table 42 only moves while a positive user input is provided. This also allows an operator to select an intermediate configuration by terminating the touch input above adjust input indicator 160 before table 42 reaches the predefined configuration.

Figure 13A:
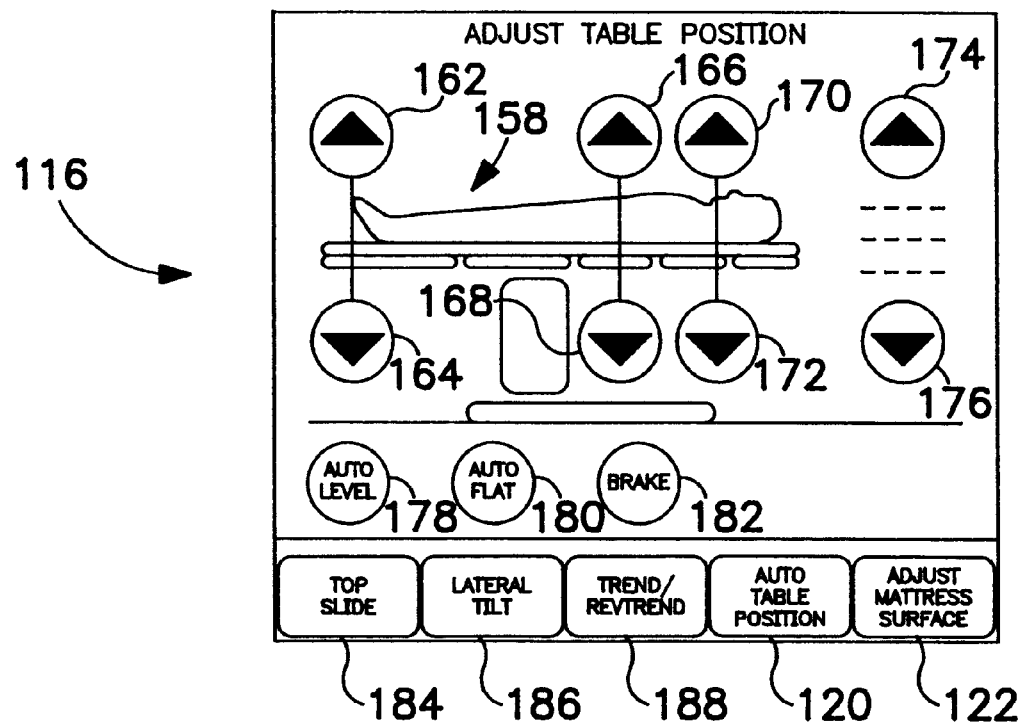
FIG. 13A is a front view of an adjust table position screen similar to FIG. 12, showing a table adjustment screen for adjusting a surgical table, including an iconographic representation of a patient atop a mattress surface and articulated table frame, with input indicators for adjusting articulated table frame sections and a vertically adjustable support column, input indicators for automatically leveling the table, automatically flattening the table surface, and engaging a floor brake, and selection indicators along the bottom of the display for accessing further adjustment screens.

Selection of the surgical table adjustment function, for example via selection indicator 118 as shown in FIGS. 9–12, results in the display of FIG. 13A. Iconographic representation 158 is provided with elements of table frame 58 and mattress 60 shown in nominal positions, along with up and down adjustment input indicators 162, 164, 166, 168, 170, 172, 174, 176, auto level input indicator 178, auto flat input indicator 180, and brake input indicator 182. Selection indicators 184, 186, 188 are provided along the bottom of display 116 for accessing top slide, lateral tilt, and Trendelenburg adjustment display screens, as are selection indicators 120, 122 for automatic table adjustment and mattress adjustment.

Up and down adjustment input indicators 162, 164, 166, 168, 170, 172, 174, 176 provide for "press and hold" adjustment of designated sections of articulated frame 58 as indicated by the graphical display and their placement relative to iconographic display 158. Up and down input indicators 162, 164 designate control of lower leg sections 94, indicators 166, 168 designate control of lower back section 88, indicators 170, 172 designate control of upper back section 86, and indicators 174, 176 designate control of vertical support column 76. Up and down adjustment of designated sections provides for fine tuning the configuration of frame 58 from any predefined configuration.

Auto level input indicator 178 provides for automatically moving all articulated sections of frame 58 to achieve a level (horizontal) configuration. Like adjust input indicator 160 discussed above, auto level input indicator 178 can be used to achieve intermediate configurations via the "press and hold" feature. Similarly, auto flat input indicator 180 provides for automatically moving all articulated sections of frame 58 to achieve a flat configuration (while maintaining any preexisting longitudinal inclination of frame 58 with respect to the ground). Brake input indicator 182 provides for locking or unlocking one or more wheels or casters (not shown) provided on base 78 of table 42 to prevent movement of table 42 along the ground.

An alternative table adjustment display somewhat similar to FIG. 13A is shown in FIG. 13B, with input indicators performing the same functions labeled with the same reference numbers. The table adjustment display of FIG. 13B displays only "high level" selection indicators 120, 122, 124 for automatic table adjustment, mattress adjustment, and help information along the bottom of display 116. Selection indicators 184, 186, 188 for table sliding, Trendelenberg tilting, and lateral tilting are displayed near auto flat 180, brake 182, and slow adjust 183 input indicators. FIG. 13B illustrates how controller 40's architecture permits reprogramming to provide a user interface as desired.

Figure 14:
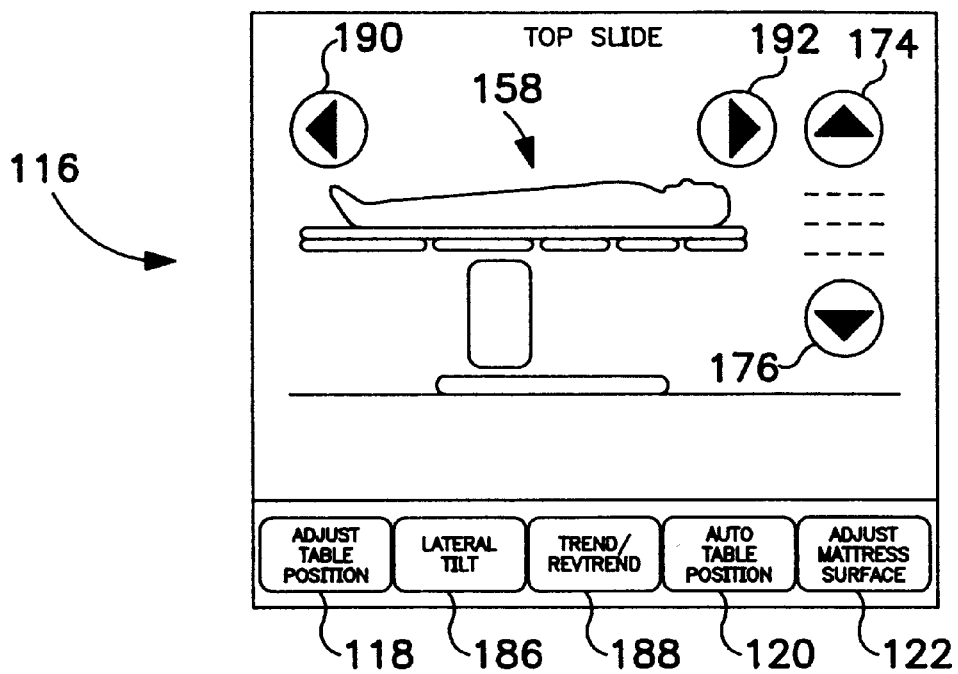
FIG. 14 is a front view of a top slide screen similar to FIG. 12, showing input indicators for sliding the table surface from end-to-end relative to the support column and for adjusting the vertical support column.

A top slide display accessible via selection indicator 184 is provided for moving table frame sections 84, 86, 88, 90, 92, 94 longitudinally relative to vertical support column 76 as shown in FIG. 14. Iconographic representation 158 is provided with frame 58 shown in a level configuration, although a representation showing a current configuration of articulated sections 84, 86, 88, 90, 92, 94 can be provided. Head end and foot end slide input indicators 190, 192 for sliding frame 58 longitudinally relative to vertical support column 76 provide "press and hold" capability as discussed above for the up and down input indicators of FIG. 13A. Vertical up and down input indicators 174, 176 are also provided on display 116, as are table adjustment, lateral tilt, Trendelenburg adjustment, automatic table adjustment, and mattress adjustment selection indicators 118, 186, 188, 120, 122.

Figure 15:
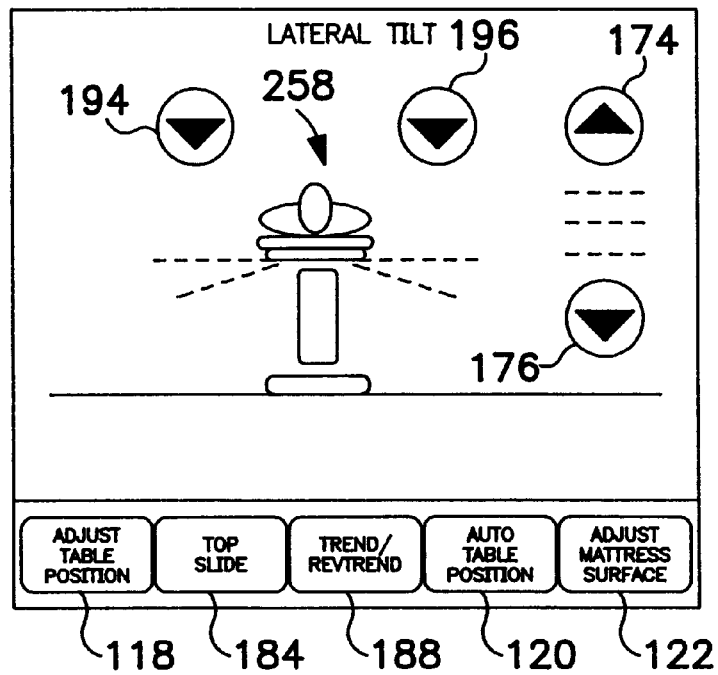
FIG. 15 is a front view of a lateral tilt screen similar to FIG. 12, showing input indicators for tilting the table about a longitudinal axis and for adjusting the vertical support column.

A lateral tilt display accessible via selection indicator 186 is provided for tilting table frame sections 84, 86, 88, 90, 92, 94 laterally relative to vertical support column 76 as shown in FIG. 15. Iconographic representation 258, which shows an end view of patient 54 atop table 42, is provided. Left and right tilt input indicators 190, 192 for tilting seat frame 58 and mattress 60 laterally relative to vertical support column 76 provide the "press and hold" capability as discussed above. Vertical up and down input indicators 174, 176 are also provided on display 116, as are table adjustment, top slide, Trendelenburg adjustment, automatic table adjustment, and mattress adjustment selection indicators 118, 184, 188, 120, 122.

Figure 16:
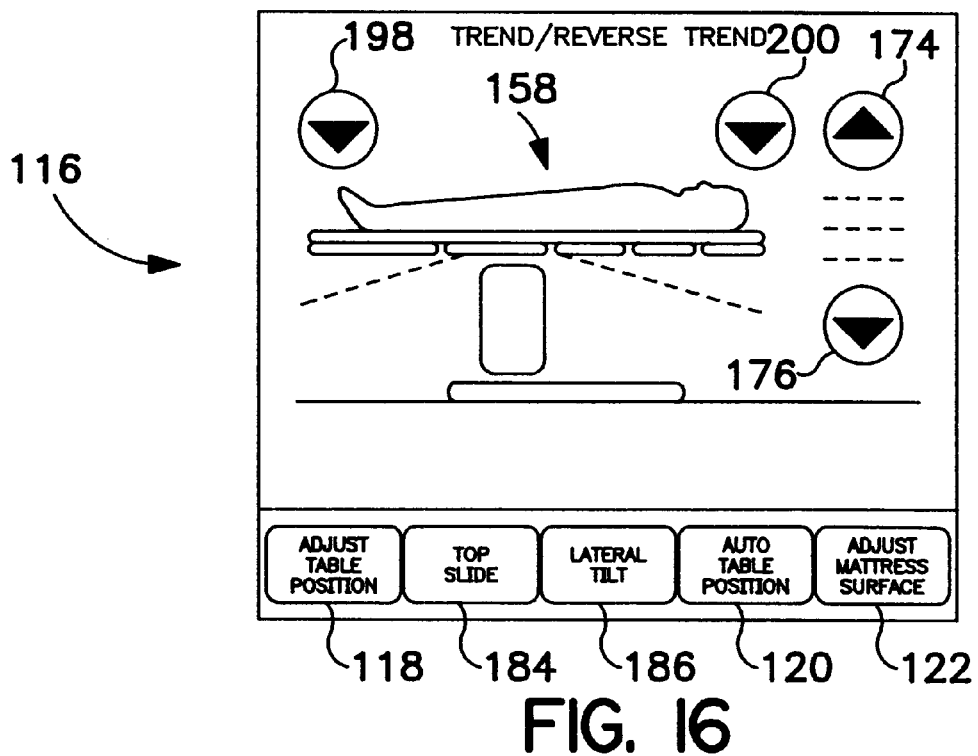
FIG. 16 is a front view of a Trendelenberg adjustment screen similar to FIG. 12, showing input indicators for tilting the table about a lateral axis and for adjusting the vertical support column.

A Trendelenburg display accessible via selection indicator 188 is provided for conjointly tilting table frame sections 84, 86, 88, 90, 92, 94 longitudinally relative to vertical support column 76 as shown in FIG. 16. Iconographic representation 158 is provided with frame 58 shown in a level configuration, although, as with the display of FIG. 14, a representation showing a current configuration of articulated sections 84, 86, 88, 90, 92, 94 can be provided. Foot end down and head end down input indicators 198, 200 for tilting frame 58 longitudinally relative to vertical support column 76 provide "press and hold" capability as discussed above. Vertical up and down input indicators 174, 176 are also provided on display 116, as are table adjustment, top slide, lateral tilt, automatic table adjustment, and mattress adjustment display selection indicators 118, 186, 188, 120, 122.

Figure 17:
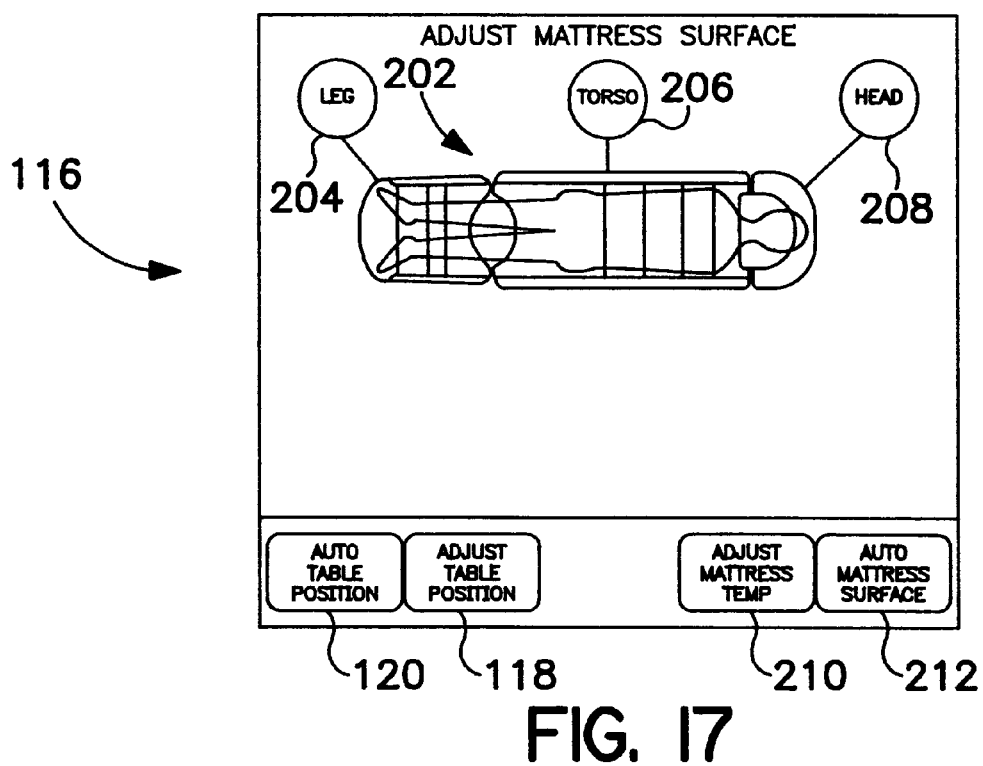
FIG. 17 is a front view of a mattress surface adjustment screen including an iconographic representation of a top view of a patient atop a mattress, with selection indicators for selecting leg, torso, and head adjustment functions, and including selection indicators along the bottom of the display to access mattress temperature adjustment and automatic mattress surface adjustment screens.

A mattress adjustment display accessible via selection indicator 122 is provided for controlling features of mattress 60 as shown in FIG. 17. A pictogram or iconographic representation 202 depicts a plan view of patient 54 atop mattress 60 showing various chambers with leg, torso, and head mattress sections. Selection indicators 204, 206, 208 are provided for selecting further screens for controlling leg 102, torso 100, and head 96, 98 sections of mattress 60. Automatic table adjustment, table adjustment, mattress temperature adjustment, and automatic mattress adjustment display selection indicators 118, 120, 210, 212 are provided near display 116 bottom.

Figure 18:
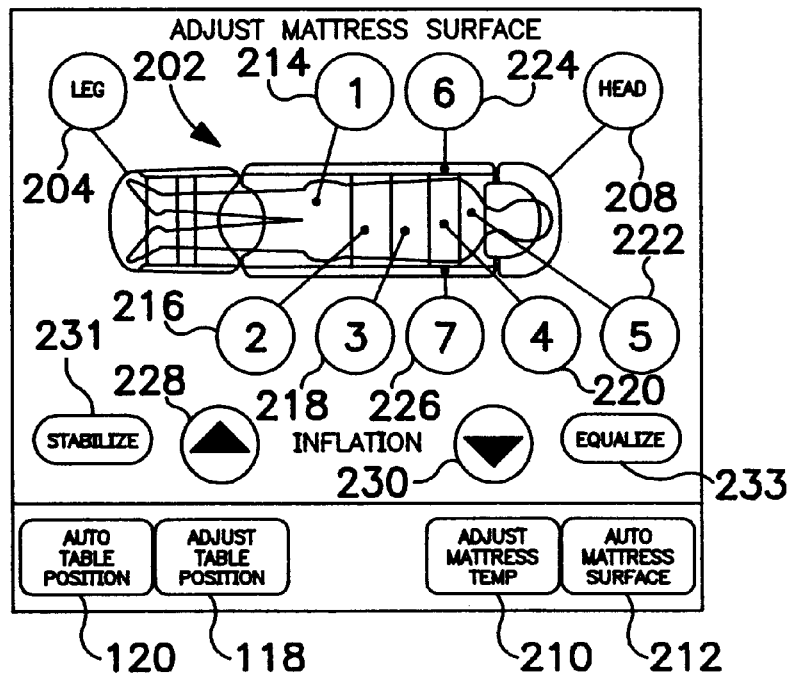
FIG. 18 is a front view of a mattress surface adjustment screen similar to FIG. 17 with a torso section of the mattress selected for adjustment, and including selection indicators for selecting regions of the torso section of the mattress for adjustment, input indicators for increasing or decreasing pressure in a selected region, and input indicators for stabilizing the mattress surface or to equalize mattress pressure.

A torso mattress adjustment display accessible via torso selection indicator 204 is provided for controlling torso section 100 of mattress 60 as shown in FIG. 18. Iconographic representation 202 and leg and head mattress section selection indicators 204, 208 are provided as shown in FIG. 17. Torso mattress section chamber selection indicators 214, 216, 218, 220, 222, 224, 226 are provided near their corresponding locations on iconographic representation 202, along with lines indicating the correspondence. One or more mattress section chambers can be selected by depressing its indicator, which results in a reverse video display of that indicator to indicate its selection. Inflation increase and decrease input indicators 228, 230 are provided for increasing or decreasing pressure in one or more selected mattress sections, using a "press and hold" paradigm as discussed above.

Stabilize input indicator 231 and equalize input indicator 233 are provided near increase and decrease input indicators 228, 230. The stabilize feature stiffens one or more selected sections of vacuum bead mattress 60 by creating a vacuum in the corresponding chamber(s) to withdraw fluid from selected section(s). The equalize feature adjusts selected mattress sections to a baseline level by setting pressure in corresponding chambers to a baseline level to prepare for a new patient or procedure. The torso mattress adjustment display also includes automatic table adjustment, table adjustment, mattress temperature adjustment, and automatic mattress adjustment selection indicators 120, 118, 210, 212 displayed along the bottom of display 116. Similar display screens (not shown) are provided for controlling leg and head sections 102, 96, 98 of mattress 60.

Figure 19:
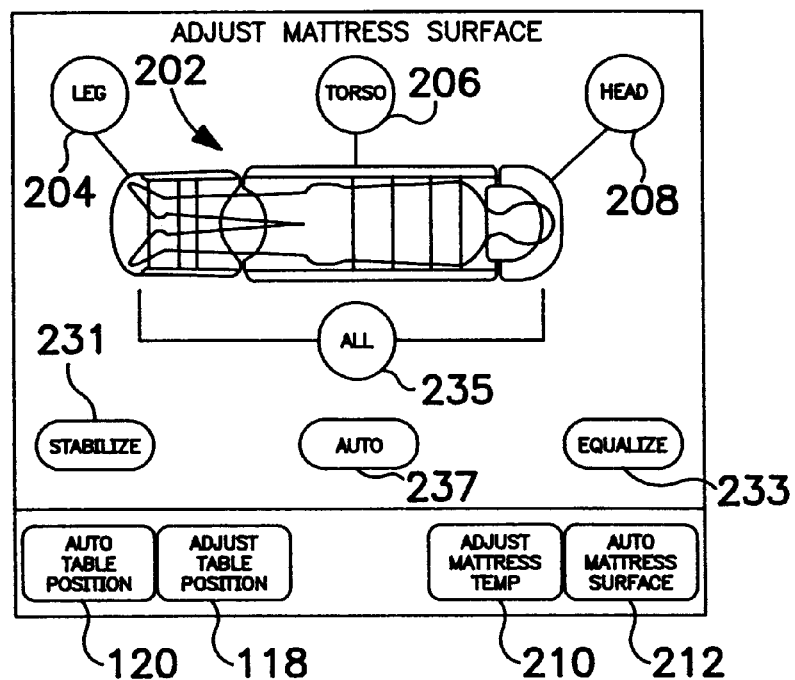
FIG. 19 is a front view of an automatic mattress surface adjustment screen similar to FIG. 17, including selection indicators for selecting some or all portions of the mattress for adjustment and input indicators for stabilizing, equalizing, or automatically adjusting the entire mattress by sensing pressure in each mattress region and controlling each region to conform the mattress to the patient's body.
Figure 20:
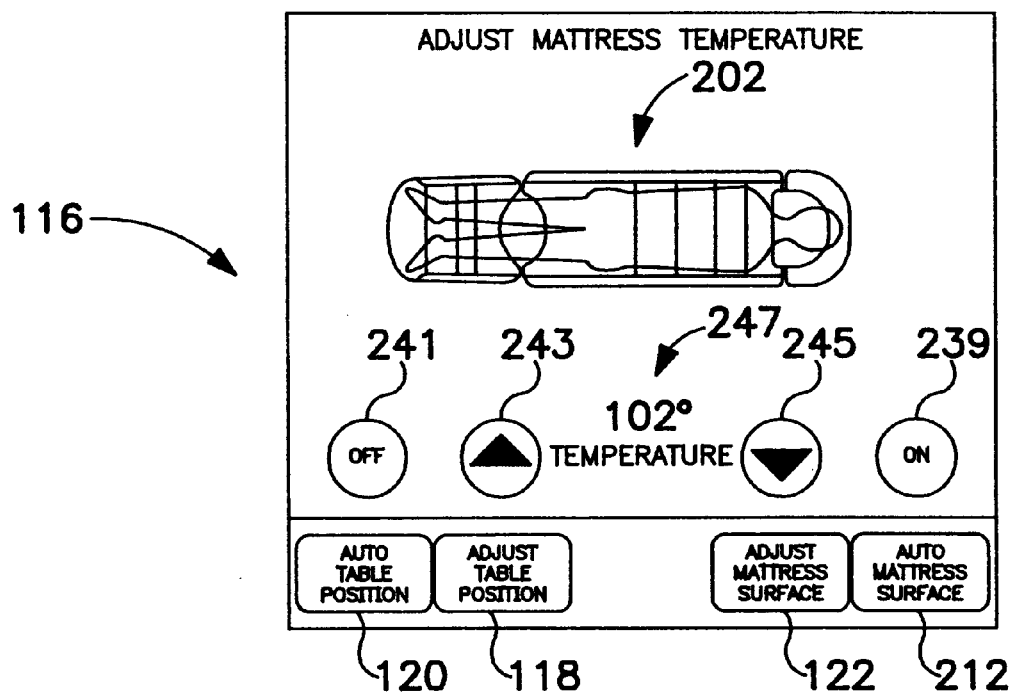
FIG. 20 is a front view of a mattress temperature adjustment screen similar to FIG. 17, including a temperature display and input indicators for enabling or disabling temperature control and for increasing or decreasing a designated temperature.

An automatic mattress adjustment display accessible via automatic mattress adjustment selection indicator 212 includes iconographic representation 202, leg, torso, and head mattress section selection indicators 204, 206, 208, an all mattress section selection indicator 235, and stabilize, equalize, and automatically adjust input indicators 231, 233, 237 as shown in FIG. 19. The all mattress selection indicator 235 provides a shorthand mechanism for selecting all sections. The stabilize and equalize functions work as discussed above for FIG. 18, except that all chambers within a selected mattress section are automatically designated for a selected mattress section. Selection of automatically adjust input indicator 237 uses pressure sensors within each chamber or cell (not shown) coupled to mattress 60 to conform mattress 60 automatically to a patient's body by varying pressures to each chamber based on sensed pressure. As with FIG. 18, automatic table adjustment, table adjustment, mattress temperature adjustment, and automatic mattress adjustment selection indicators 120, 118, 210, 212 displayed along the bottom of display 116.

A mattress temperature adjustment display accessible via mattress temperature adjustment selection indicator 210 includes iconographic representation 202, temperature subsystem on and off buttons 239, 241 for enabling or disabling the temperature control subsystem, target temperature increase and decrease input indicators 243, 245, and a target temperature display value 247. This display illustrates control of an optional temperature control subsystem (not shown) that controls the entire mattress temperature to a particular target value, such as by using a temperature controlled fluid supply to the mattress, a thermal-resistive covering of the mattress, etc. Those skilled in the art will understand that further temperature control features can be provided, such as separate temperature control for different mattresses regions or sections, display of actual temperature(s) of the mattress surface, facilities for cycling temperature over various periods and ranges, etc. This highlights a basic advantage of controller 40's architecture, which facilitates integration of additional features or controlled subsystems into a single interface.

Controller 40 further provides for programming and storing desired configurations of table frame 58 and mattress 60 for subsequent recall from auto adjust menu 132. A "save config" input indicator (not shown) provided from appropriate display screens such as the adjust table screens of FIGS. 13A and 13B provides access to a "save named configuration" screen (not shown) that prompts the user for entry of a configuration name through use of an alphabetic keypad provided on display 116. Management functions for manipulating saved configurations further provide for deleting, renaming, reordering, etc. of stored configurations.

Referring now to FIGS. 22–24, controller 40 is designed to support its use by either a left-handed or right-handed operator. An essentially "ambidextrous" device is provided by housing 114 and display 116 that are substantially symmetric about a longitudinal axis 261 of controller 40. Housing 114 has relatively flat front and back surfaces 249, 251 coupled by rounded side edges 253, bottom edge 263, and top edge 265. Display 116 and power button 115 are coupled to front surface 249. As best shown in FIGS. 23 and 24, display 116 covers most of front surface 249 of housing 114 so that a relatively large display with large, easy-to-see touch-screen buttons are provided in a portable, hand-held unit.

Housing 114 includes a handle 255 appended to back surface 251. Handle 255 is configured with a cylindrical shape having a somewhat elliptical cross-section to facilitate ease of grasping and holding. Handle 255 is configured to retain rechargeable batteries (not shown) that provide power for controller 40. The cylindrical shape of handle 255 further facilitates coupling controller 40 to a retaining socket (not shown) for temporary or permanent storage. The retaining socket can be provided on an IV pole, equipment bracket, or wall, or anywhere in an operating room environment, and is configured to provide for battery recharging either with a direct voltage coupling or through an indirect magnetic field charging system. Handle 255 further provides a support to allow for sitting controller 40 upright by placing controller bottom surface 263 on a table or other surface. Although a generally cylindrical handle 255 is shown, those skilled in the art will see the abundance of variations possible for configuring alternative handles to facilitate holding controller 40 and coupling it to items found throughout the operational environment, such as an operating room, to facilitate temporary or permanent storage of controller 40.

Figure 27:
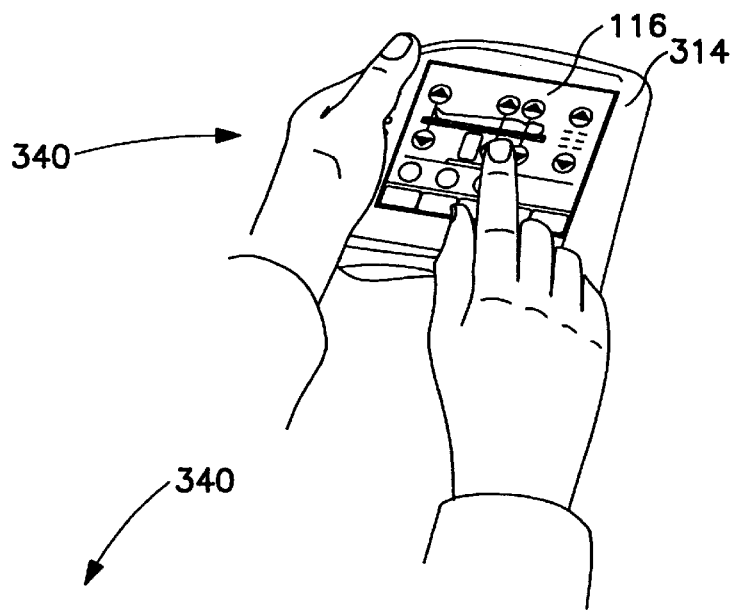
FIG. 27 is a perspective view of the controller of FIG. 22 showing a right-handed user interface.
Figure 25:
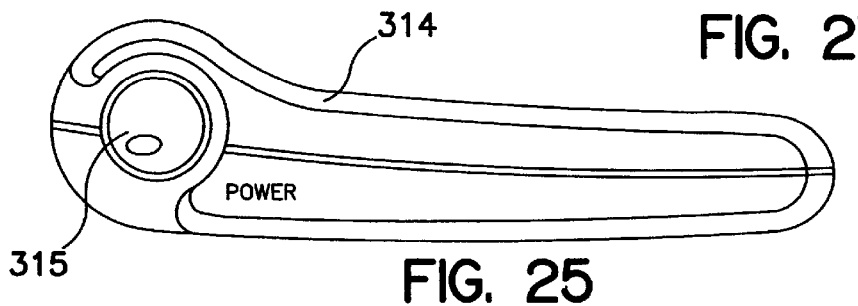
FIG. 25 is a top plan view of another embodiment of a medical device controller similar to the embodiment of FIGS. 9–11, showing a housing profile with a power button and configured for holding by a left hand.
Figure 26:
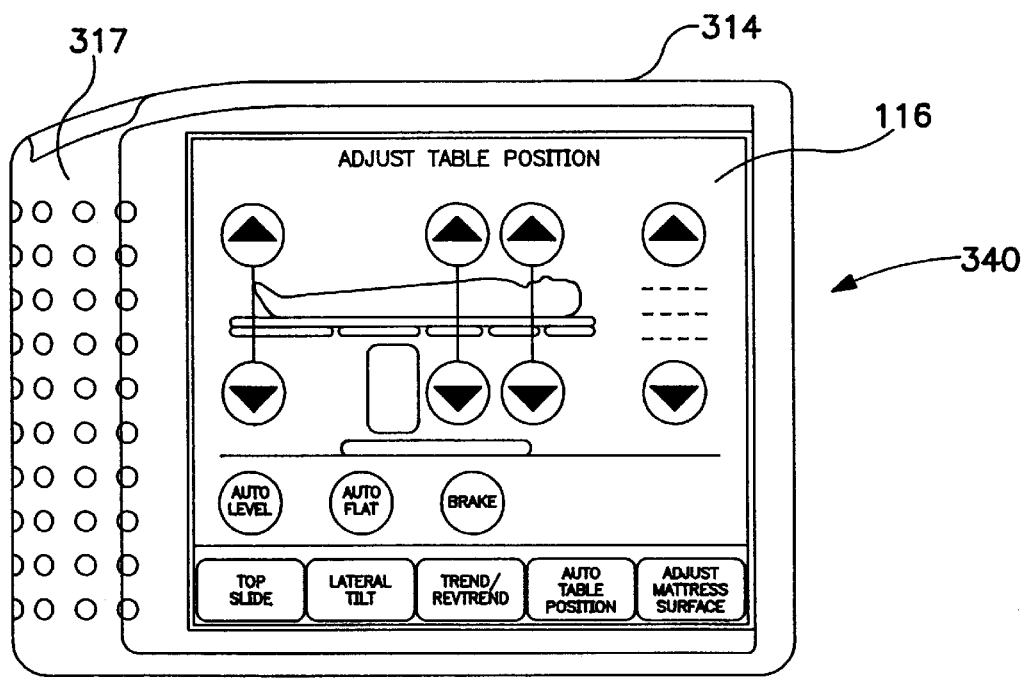
FIG. 26 is a front elevation view of the controller of FIG. 22, showing a gripping surface and a display.
Figure 28:
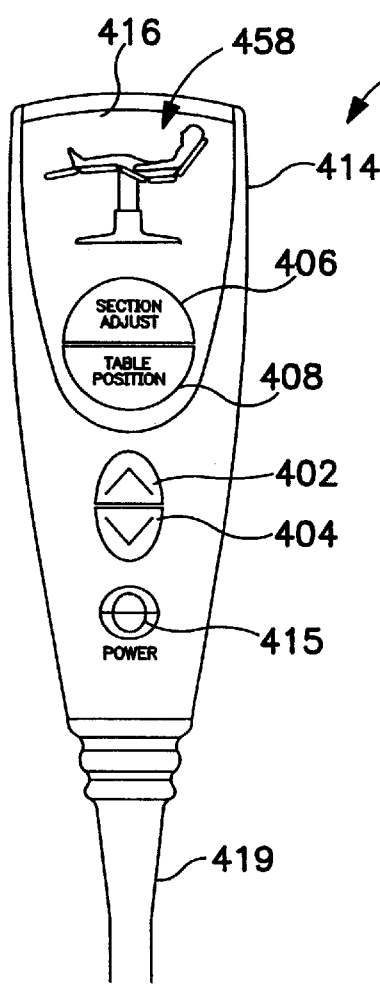
FIG. 28 is a front elevation view of another embodiment of a medical device controller, showing a tapered housing with a graphical display, semi-circular adjust and select buttons, a pair of up/down buttons, and a recessed power button, each button aligned along a central vertical axis of the housing to facilitate ambidextrous use of the controller.
Figure 29:
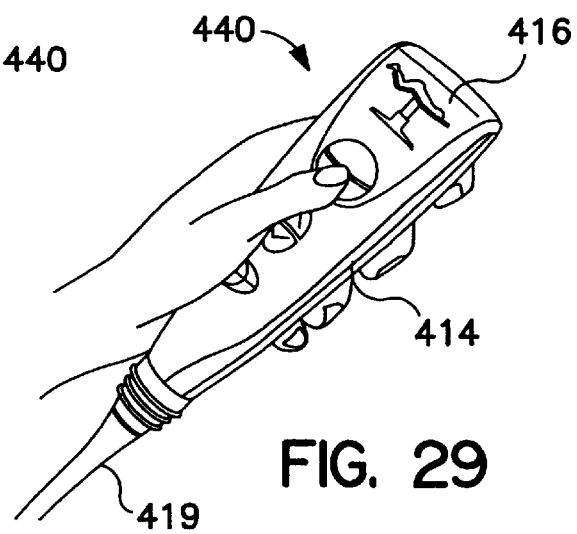
FIG. 29 is a perspective view of the controller of FIG. 28 showing left-handed use of the controller.
Figures 30, 31:
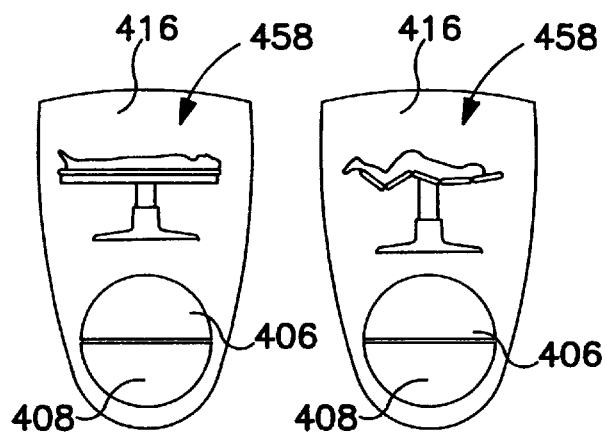
FIGS. 30–33 are front views of the display and the select and adjust buttons of the controller of FIG. 28, showing automatic configuration selection displays similar to the configurations of FIGS. 3–6.
Figures 32, 33:
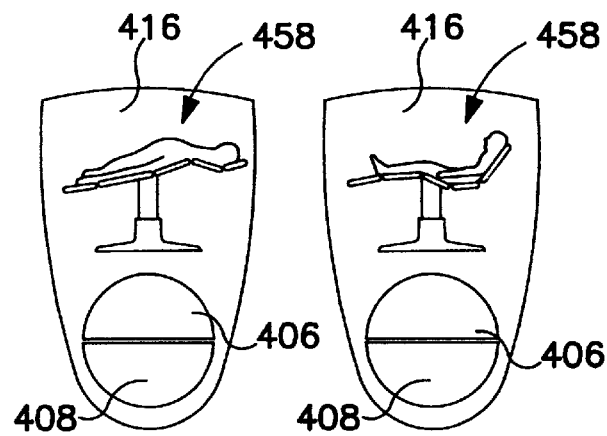
Figure 34:
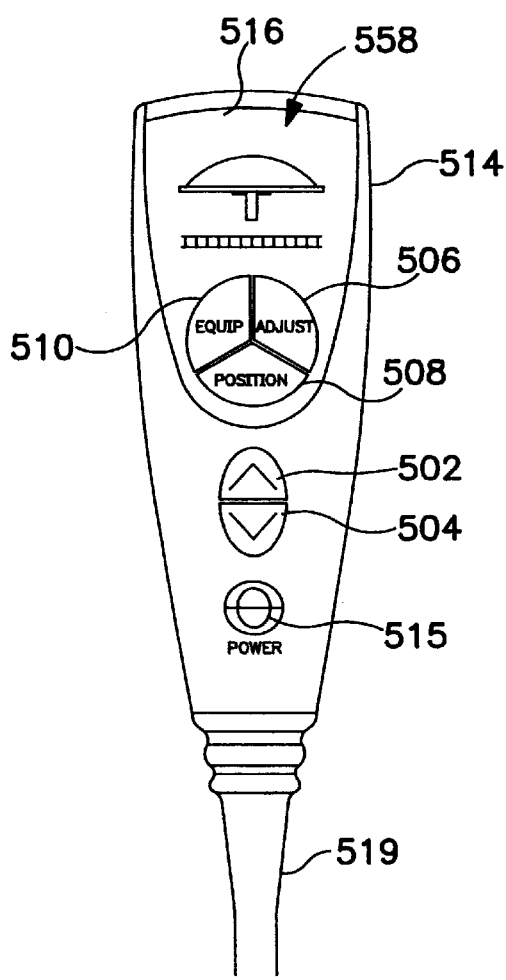
FIG. 34 is a front elevation view of another embodiment of a medical device controller similar to that of FIG. 28, showing a tapered housing with a graphical display, three pie-shaped selection buttons, a pair of up/down buttons, and a recessed power button.
Figure 35:
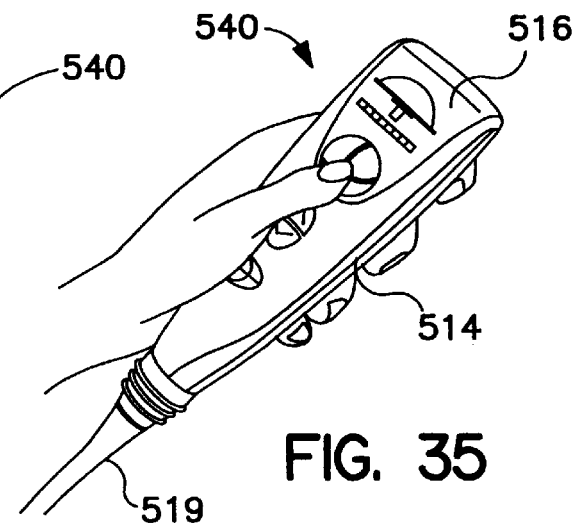
FIG. 35 is a perspective view of the controller of FIG. 24 showing left-handed use of the controller.

Referring now to FIGS. 25–27, an alternative embodiment controller 340 is provided that includes the same display 116 as controller 40, mounted in an asymmetric housing 314 and having a side-mounted power button 315. Controller 340 includes a left-handed gripping surface 317 so that operation of touch-screen buttons is made by a care giver's right hand. Controller 340 can, however, be programmed so that all screens are displayed "upside down", thus converting controller 340 from a right-handed configuration to a left-handed configuration. This shows the utility of the programmable architecture of the present invention.

Another alternative embodiment controller 440 is shown in FIGS. 28–33. Controller 440 includes a tapered housing 414 coupled to recessed power button 415, up and down buttons 402, 404, semi-circular adjust and select buttons 406, 408, a display 416, and a control cable 419. Like controller 40, housing 414 and display 416 are substantially symmetric about a longitudinal axis to permit equally simple use by left-handed or right-handed operators. Rather than using a touch-screen display, controller 440 uses only the four input buttons 402, 404, 406, 408, and varies the functions performed by these buttons based on the information presented and selected on display 416.

Controller 440 indicates a single selection of an item on display 416, such as a single controllable feature, a predefined overall configuration of a controlled system, or another controller option. Controller 440 provides for slewing designation of the selected item to other selectable items based on user input to select button 408. Pressing adjust button 406 when a predefined overall configuration is designated, such as one of the table configurations illustrated in FIGS. 30–33, results in controller 440 commanding the controlled system to assume the predefined configuration. As with controller 40, adjust button 406 can provide a "press and hold" capability. Pressing adjust button 406 when a controllable feature is designated allows for use of up and down buttons 402, 404 to control the designated feature, such as moving a particular section of an articulated surface, or controlling pressure of a portion of a controllable mattress, etc. Pressing adjust button 406 when another controller option is designated will result in controller 440's displaying of another display screen with selectable items.

Figures 36, 37:
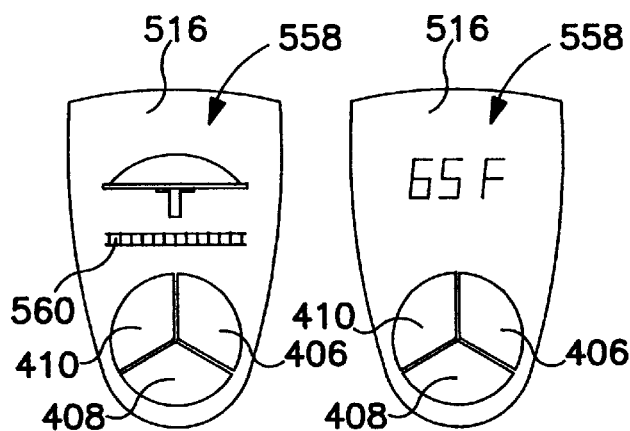
FIGS. 36–38 are front views of the display and selection buttons of the controller of FIG. 28, showing graphical interfaces for controlling a lighting system, a temperature control system, and a table.
Figure 38:
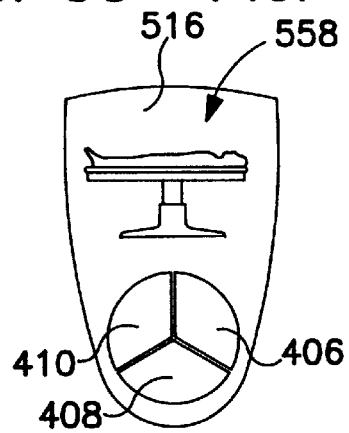

Yet another alternative embodiment controller 540 is shown in FIGS. 34–38. Controller 540 includes a tapered housing 514 coupled to recessed power button 415, up and down buttons 402, 404, pie-shaped adjust, select, and equipment buttons 506, 508, 510, a display 516, and a control cable 519. Like controllers 40 and 440, housing 514 and display 516 are substantially symmetric about a longitudinal axis to permit equally simple use by left-handed or right-handed operators. Controller 540's display 516 is the same as display 416, with controller 540 similarly programmed to provide information on display 516, such as an iconographic representation 558, along with other indicia indicating controllable features and other selectable controller menu options. Iconographic representation 558 varies to represent the controlled system by displaying a stylized lighthead as shown in FIG. 36, temperature display as shown in FIG. 37, and surgical table as shown in FIG. 37. A light intensity indicator bar 560 is provided as shown in FIG. 36, which varies an amount displayed in reverse video to represent the percentage light intensity currently being output by the lighthead. Similarly, the temperature display of FIG. 37 is updated to indicate an actual controlled temperature value, and the iconographic table representation of FIG. 38 is presented in correspondence with the current surgical table configuration.

Operation of controller 540 is the same as for controller 440 except that controller 540 includes equipment button 510, which is used to switch between different controlled systems. Thus, rather than selecting a displayed item to switch between controlled systems, controller 540 automatically toggles between controlled systems when an operator presses equipment button 510. This provides a convenient mechanism for quickly switching via single press of a button to a desired system, such as the lighting system of FIG. 36, the temperature control system of FIG. 37, and the table system of FIG. 38.

Yet another alternative embodiment controller 640 includes a hand-held housing 614, a display 616, eight pairs of buttons 650 . . . 680, and a power button 682 as shown in FIGS. 39–40. Controller 640, including its buttons 650 . . . 682, is symmetric about a longitudinal axis 661 to facilitate ambidextrous use. Buttons 650 . . . 680 include indicia that represent their respective table control functions and provide "press and hold" control as discussed above. Buttons 650, 652 provide a table high/low functions, buttons 654, 656 provide Trendelenberg/Reverse Trendelenberg functions, buttons 658, 660 provide lateral tilt left/right functions, buttons 662, 664 provide back up/down functions, buttons 666, 668 provide upper back up/down functions, buttons 670, 672 provide leg up/down functions, buttons 674, 676 provide slide lower/upper functions, button 678 provides an auto flat function, and button 680 provides a high speed button to increase table speed when depressed simultaneously with another of buttons 650 . . . 678. Controller 640 provides a sealed housing that is durable, easy to clean, and suitable for use in sterile environments. Buttons 650 . . . 680 are backlit to enhance ease of use, and display 616 provides graphic functionality similar to controllers 40, 340, 440, 540 discussed above. Controller 640 can be a pendant controller tethered to table 42 similar to controller 81 of FIG. 2 or can be configured as a wireless controller.

A controller according to the present invention thus provides a single, handheld control unit that can operate multiple medical devices, such as both a surgical table and a mattress system. The controller permits both wireless operation or a conventional cable system. A display is provided, such as a relatively large, backlit display, that is easy to see and understand, and provides a friendly user-interface without using small buttons. Touch-screen display 116 preferably is flat, easy to clean, and durable. The controller provides a menu driven system that effectively displays to a user the information necessary for any given adjustment of a controlled system, thus optimizing the ease and effectiveness of its use. The use of named, predefined configurations, such as for surgical table 42 in automatic adjustment menus 132, 232, allows for personalized care giver and procedure names, as well as for "single button set-up" of a complex system. Integrated help, operating, and servicing displays further enhance the ease of use and utility of a controller according to the present invention.

Although the invention has been described in detail with reference to certain preferred embodiments, variations and modifications exist within the scope and spirit of the present invention as described and defined in the following claims.

What is claimed is:

1. A patient support system comprising:
    an articulated frame having a plurality of segments movable relative to each other to position the articulated frame in a plurality of different frame configurations;
    a frame controller coupled to the frame to move at least one of the segments;
    a mattress having at least one chamber and being adjustable to a plurality of different mattress configurations;
    a mattress controller coupled to the mattress to control an amount of fluid in the at least one chamber; and
    a user interface controller including a screen to display information, the screen having a plurality of input portions configured to receive inputs from an operator, the user interface controller being configured to send control signals to the frame controller and to the mattress controller in response to the inputs received by the input portions of the screen.

2. The system of claim 1, wherein the screen of the user interface controller comprises a touch-screen display configured to display an iconographic representation of the articulated frame and to generate the control signals.

3. The system of claim 2, wherein the user interface controller further includes a processor coupled to the screen, the processor being configured to provide indicia on the screen indicative of a user input to move the plurality of segments of the articulated frame to a desired frame configuration, the processor being further configured to provide indicia on the display indicative of a user input to adjust the mattress to a desired mattress configuration.

4. The system of claim 1, wherein the user interface controller includes a processor configured to provide a menu on the screen of a plurality of predefined configurations of the articulated frame, the processor being configured to command the articulated frame to move to a selected one of a plurality of predefined configurations based on a user input.

5. The system of claim 4, wherein the menu includes a plurality of named positions that correspond to predefined configurations.

6. The system of claim 4, wherein the user interface controller includes means for programming and storing the plurality of predefined configurations of the articulated frame.

7. The system of claim 4, wherein the user interface controller is configured to provide the iconographic representation on the screen indicative of the articulated frame.

8. The system of claim 1, further comprising a lighting system having at least one light head, and a lighting controller coupled to the lighting system to control an intensity of light from the at least one light head, and wherein the user interface controller is also configured to send control signals to the lighting controller.

9. The system of claim 1, further comprising a patient thermal regulation system, and a thermal regulation controller coupled to the patient thermal regulation system, and wherein the user interface controller is also configured to send control signals to the thermal regulation controller.

10. An patient support system comprising:
   an articulated table having a plurality of segments;
   a table controller coupled to the table to move at least one of the segments;
   a lighting system having at least one light head;
   a lighting controller coupled to the lighting system to control an intensity of light from the at least one light head; and
   a user interface controller configured to send control signals to the table controller and to the lighting controller.

11. The system of claim 10, wherein the user interface controller includes a touch-screen display configured to display an iconographic representation of the articulated table and to generate the control signals.

12. The system of claim 11, wherein the user interface controller further includes a processor coupled to the display, the processor being configured to provide indicia on the display indicative of a user input to move the plurality of segments of the articulated table to a desired table configuration.

13. The system of claim 10, wherein the user interface controller includes a display and a processor configured to provide a menu on the display of a plurality of predefined configurations of the articulated table, the processor being configured to command the articulated table to move to a selected one of a plurality of predefined configurations based on a user input.

14. The system of claim 13, wherein the menu includes a plurality of named positions that correspond to predefined configurations.

15. The system of claim 13, wherein the user interface controller includes means for programming and storing the plurality of predefined configurations of the articulated table.

16. The system of claim 13, wherein the user interface controller is configured to provide the iconographic representation on the display indicative of the articulated table.

17. The system of claim 10, further comprising a mattress having at least one chamber, and a mattress controller coupled to the mattress to control an amount of fluid in the at least one chamber, and wherein the user interface controller is also configured to send control signals to the mattress controller.

18. The system of claim 17, further comprising a patient thermal regulation system, and a thermal regulation controller coupled to the patient thermal regulation system, and wherein the user interface controller is also configured to send control signals to the thermal regulation controller.

19. The system of claim 10, further comprising a patient thermal regulation system, and a thermal regulation controller coupled to the patient thermal regulation system, and wherein the user interface controller is also configured to send control signals to the thermal regulation controller.

20. A patient support system comprising:
   an articulated frame having a plurality of segments;
   a frame controller coupled to the frame to move at least one of the segments;
   a mattress having at least one chamber;
   a mattress controller coupled to the mattress to control an amount of fluid in the at least one chamber; and
   a user interface controller configured to send control signals to the frame controller and to the mattress controller, the user interface controller including a display and a processor configured to selectively provide a plurality of different menus on the display, each of the menus including a plurality of predefined configurations of the articulated frame, the processor being configured to command the articulated frame to move to a selected one of a plurality of predefined configurations based on a user input.

21. The patient support system of claim 20, wherein the display is a touch-screen display configured to display information and receive user input.

22. The system of claim 20, wherein a menu includes a plurality of named positions that correspond to predefined configurations.

23. The system of claim 20, wherein the user interface controller includes means for programming and storing the plurality of predefined configurations of the articulated frame.

24. The system of claim 20, wherein the user interface controller is configured to provide the iconographic representation on the display indicative of the articulated frame.

25. The patient support system of claim 20, wherein a first menu is configured to control the frame controller and a second menu is configured to control the mattress controller.

26. The patient support system of claim 20, wherein the information on the display of the user interface controller is displayed in a predefined format.

27. The patient support system of claim 26, wherein the user interface controller is configured to modify the predefined format to display information on the display in a modified format.

28. The patient support system of claim 26, wherein the user interface controller is configured to create a plurality of formats for displaying information on the display.

29. A patient support system comprising:
   a base;
   an articulated frame coupled to the base, the articulated frame having a plurality of segments movable relative to each other to position the frame in a plurality of different frame configurations;
   a frame controller coupled to the frame to move at least one of the segments;
   a user interface controller including a screen configured to display a plurality of variable indicia each indicative of a user command to move the articulated frame to a desired frame configuration, and a plurality of user input portions each associated with one of the variable indicia and configured to send a control signal to the frame controller to move the articulated frame to the desired frame configuration in response to a user input.

30. The patient support system of claim 29, wherein the user input portions form part of the screen.

31. The system of claim 29, wherein the user interface controller includes a processor configured to provide a menu on the screen of a plurality of predefined configurations of the articulated frame, the processor being configured to command the articulated frame to move to a selected one of a plurality of predefined configurations based on a user input.

32. The system of claim 31, wherein the menu includes a plurality of named positions that correspond to predefined configurations.

33. The system of claim 31, wherein the user interface controller includes means for programming and storing the plurality of predefined configurations of the articulated frame.

34. The system of claim 29, wherein the user interface controller is configured to provide an iconographic representation on the screen indicative of the articulated frame.

* * * * *